US012780807B2

(12) United States Patent
Shin et al.

(10) Patent No.: US 12,780,807 B2
(45) Date of Patent: Nov. 3, 2026

(54) DIPHENAZINE COMPOUND, AND USE THEREOF FOR PREVENTING OR TREATING CANCER OR NEUROINFLAMMATORY DISEASES

(71) Applicant: KOREA INSTITUTE OF OCEAN SCIENCE & TECHNOLOGY, Busan (KR)

(72) Inventors: Hee Jae Shin, Busan (KR); Hwa Sun Lee, Busan (KR)

(73) Assignee: KOREA INSTITUTE OF OCEAN SCIENCE & TECHNOLOGY, Busan (KR)

( * ) Notice: Subject to any disclaimer, the term of this patent is extended or adjusted under 35 U.S.C. 154(b) by 355 days.

(21) Appl. No.: 18/565,708

(22) PCT Filed: Dec. 10, 2021

(86) PCT No.: PCT/KR2021/018714
§ 371 (c)(1),
(2) Date: Nov. 30, 2023

(87) PCT Pub. No.: WO2023/106464
PCT Pub. Date: Jun. 15, 2023

(65) Prior Publication Data

US 2024/0279204 A1 Aug. 22, 2024

(30) Foreign Application Priority Data

Dec. 9, 2021 (KR) ........................ 10-2021-0175850

(51) Int. Cl.

| | |
|---|---|
| ***C07D 403/06*** | (2006.01) |
| ***A23L 33/10*** | (2016.01) |
| ***A61K 31/498*** | (2006.01) |
| ***A61P 25/00*** | (2006.01) |
| ***A61P 35/00*** | (2006.01) |
| ***C07D 241/46*** | (2006.01) |
| ***C07D 403/12*** | (2006.01) |
| ***C12N 1/14*** | (2026.01) |
| ***C12P 17/12*** | (2006.01) |
| ***C12R 1/645*** | (2006.01) |

(52) U.S. Cl.
CPC .......... *C07D 403/06* (2013.01); *A61K 31/498* (2013.01); *A61P 25/00* (2018.01); *A61P 35/00* (2018.01); *C07D 241/46* (2013.01); *C07D 403/12* (2013.01); *A23L 33/10* (2016.08); *A23V 2002/00* (2013.01); *A23V 2200/308* (2013.01); *A23V 2200/322* (2013.01); *A23V 2250/30* (2013.01); *C12N 1/14* (2013.01); *C12P 17/12* (2013.01); *C12R 2001/645* (2021.05)

(58) Field of Classification Search
None
See application file for complete search history.

(56) References Cited

FOREIGN PATENT DOCUMENTS

| | | |
|---|---|---|
| KR | 1020000049252 A | 7/2000 |
| KR | 102120907 B | 6/2020 |

OTHER PUBLICATIONS

Laursen et. al. ((2004), Phenazine Natural Products: Biosynthesis, Synthetic Analogues, and Biological Activity, Chem. Rev., 104, 1663-1685) (Year: 2004).*
Garg, Rajni, William A. Denny, and Corwin Hansch. "Comparative QSAR studies on substituted bis-(acridines) and bis-(phenazines)-carboxamides: a new class of anticancer agents." Bioorganic & medicinal chemistry 8.7 (2000): 1835-1839.
Laursen, Jane B., et al. "Solid-phase synthesis of new saphenamycin analogues with antimicrobial activity." Bioorganic & medicinal chemistry letters 12.2 (2002): 171-175.
Lee, Hwa-Sun, et al. "Phenazine derivatives with anti-inflammatory activity from the deep-sea sediment-derived yeast-like fungus *Cystobasidium laryngis* IV17-028." Marine drugs 17.8 (2019): 482.
Spicer, Julie A., et al. "Bis (phenazine-1-carboxamides): Structure-activity relationships for a new class of dual topoisomerase I/II-directed anticancer drugs." Journal of Medicinal Chemistry 43.7 (2000): 1350-1358.
Spicer, Julie A., et al. "Synthesis and evaluation of unsymmetrical bis (arylcarboxamides) designed as topoisomerase-targeted anticancer drugs." Bioorganic & medicinal chemistry 10.1 (2002): 19-29.

* cited by examiner

*Primary Examiner* — Juliet C Switzer
*Assistant Examiner* — Dawanna Shar-Day White
(74) *Attorney, Agent, or Firm* — CANTOR COLBURN LLP

(57) ABSTRACT

The present invention provides a novel diphenazine compound or an enantiomer or pharmaceutically acceptable salt thereof. A novel diphenazine compound or an enantiomer or pharmaceutically acceptable salt thereof according to the present invention has an excellent prophylactic or therapeutic effect against the above-mentioned types of cancer by exhibiting cytotoxicity against human cancer cell lines and inhibiting the growth of cancer cells, and has an excellent prophylactic or therapeutic effect against the above-mentioned types of neuroinflammatory diseases by exhibiting the neuroinflammation inhibitory activity of microglia in LPS-induced inflammation experiments.

13 Claims, 11 Drawing Sheets

1 2 3 4 5 6

【FIG. 3】
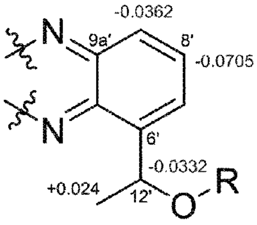
$\Delta\delta_H$ (1a-1b)
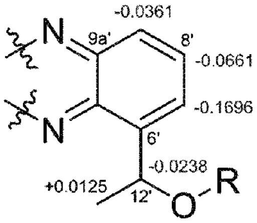
$\Delta\delta_H$ (2a-2b)
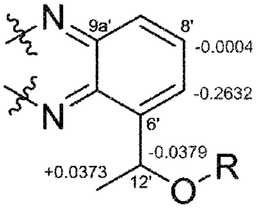
$\Delta\delta_H$ (4a-4b)
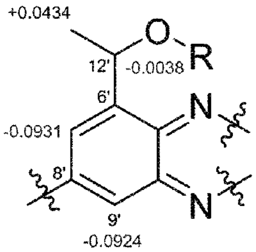
$\Delta\delta_H$ (5a-5b)
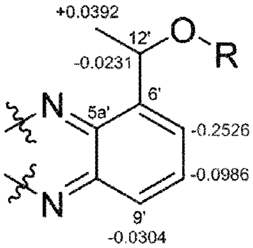
$\Delta\delta_H$ (6a-6b)
a; R = (*S*)-MTPA ester
b; R = (*R*)-MTPA ester 【FIG. 4】
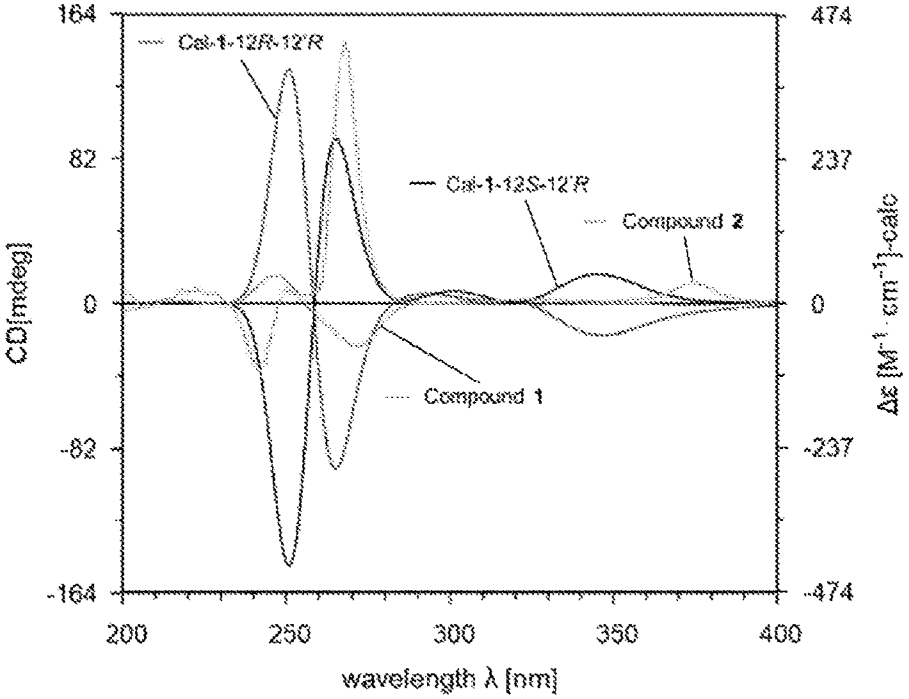

【FIG. 5】
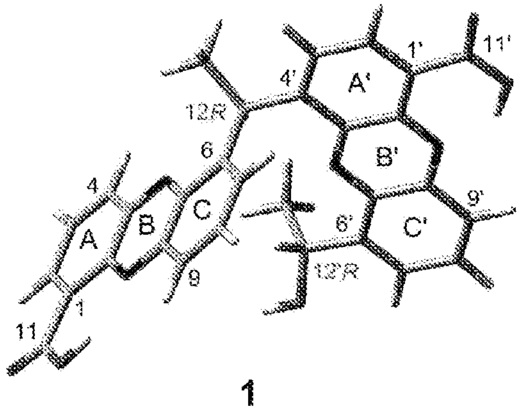
1
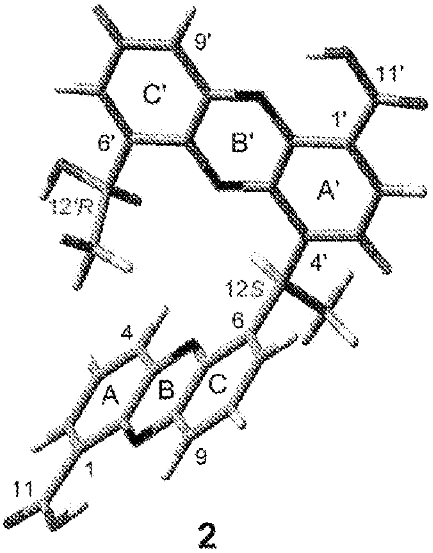
2

【FIG. 6】
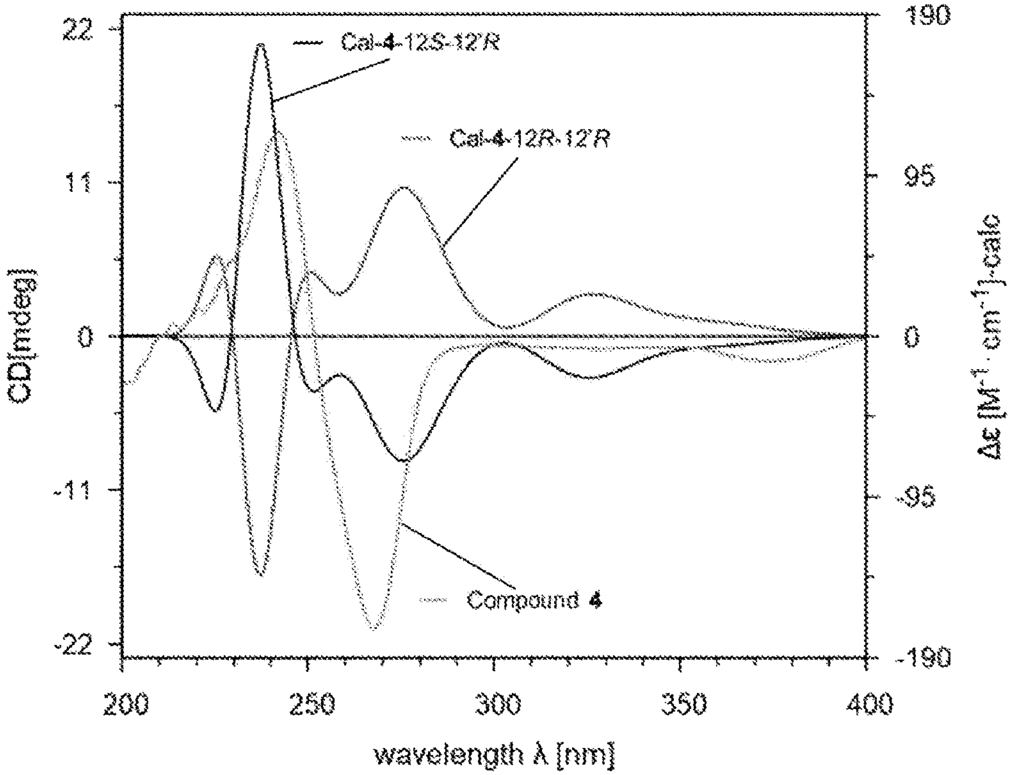

【FIG. 7】
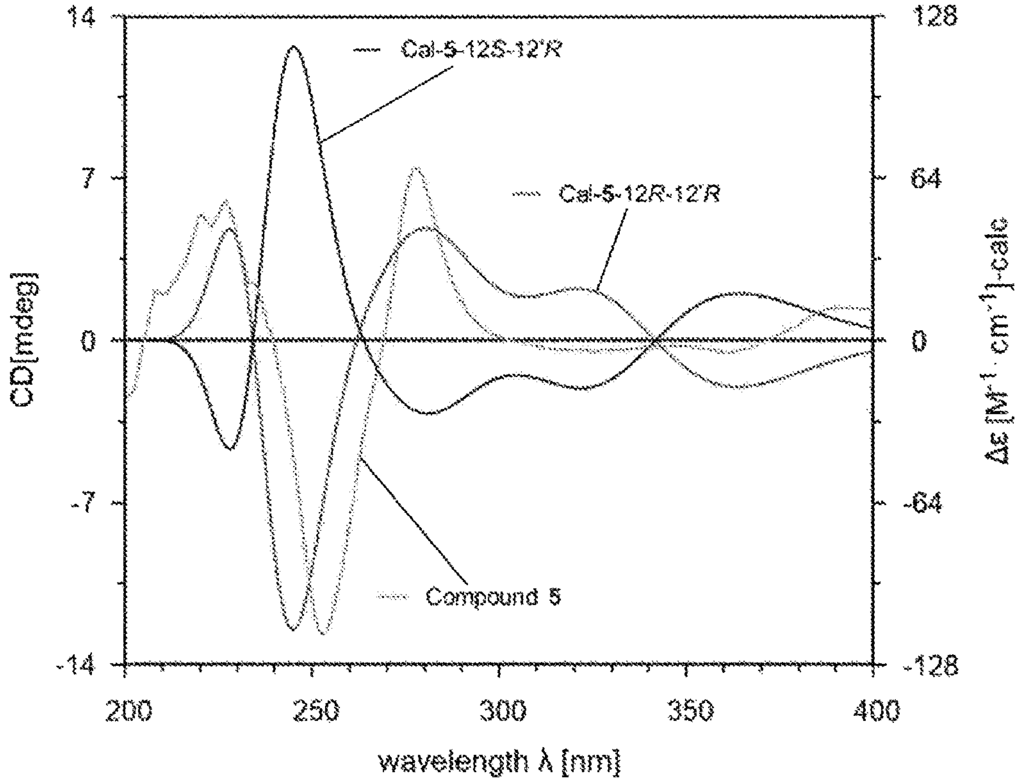

8 synthetic 6 side product 7

Fig. 11
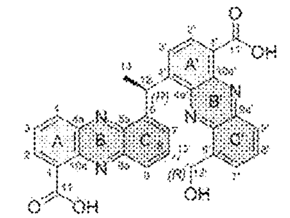
1
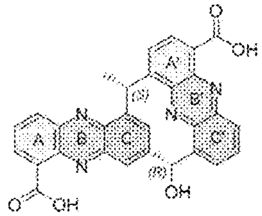
2
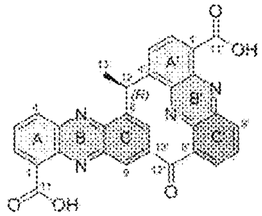
3
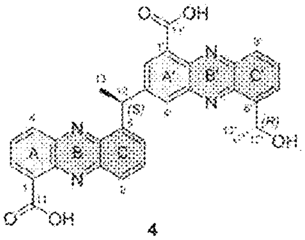
4
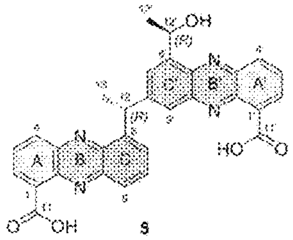
5
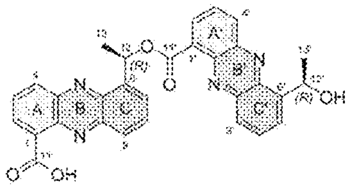
6
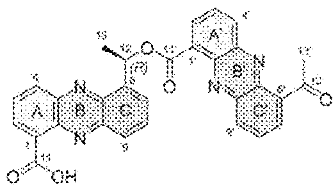
7
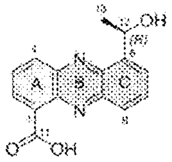
8
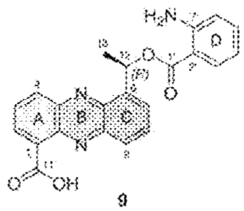
9

DIPHENAZINE COMPOUND, AND USE THEREOF FOR PREVENTING OR TREATING CANCER OR NEUROINFLAMMATORY DISEASES

CROSS REFERENCE TO RELATED APPLICATIONS

This application is a US National Stage application of PCT/KR2021/018714, filed Dec. 10, 2021, which claims the benefit of Korean Patent Application No. 10-2021-0175850 filed on Dec. 9, 2021, both of which are incorporated by reference in their entirety herein.

TECHNICAL FIELD

The present invention relates to a novel diphenazine compound and use thereof.

BACKGROUND ART

Marine fungi have been steadily studied and are known to produce a large number of new compounds. While conducting research to find novel bioactive substances derived from deep-sea microorganisms, the present inventors discovered the uncommon yeast-like fungus *Cystobasidium laryngis* IV17-028, isolated from the Indian Ocean Ridge. In the previous literature (*Mar. Drugs,* 2019, 17, 482), it was reported that three new phenazine-based derivatives were isolated from a strain IV17-028, and these derivatives showed anti-inflammatory activity in LPS-stimulated RAW 264.7 cells. Phenazine-based compounds were known to be produced by bacteria (*Streptomyces* and *Pseudomonas*) and some archaea, until they were isolated from the strain *C. laryngis* IV17-028. Phenazine skeletons having redox activity are involved with electron shuttles, reducing reactive oxygen species, controlling gene expression, biofilm formation, quorum sensing signals, maintaining intracellular redox homeostasis, and the like. Accordingly, phenazine-based compounds have received attention because of their diverse roles and the wide range of physiological activities mentioned above. Particularly, phenazine dimers (dimeric phenazine) such as esmeraldines A-B, phenazostatins A-D, izumiphenazines A-B, phenaziolins A-E, and diastaphenazine have been reported relatively less frequently, and others than phenazostatin D (reported in *pseudonocardia* species) are reported to be isolated only from *Streptomyces* species. Among the reported phenazine dimers, phenazostatins A-C have been reported to protect neuronal hybridoma N-18-RE-105 cells from glutamate toxicity for preventing brain ischemia injury.

The present inventors isolated phenazostatins E-J and determined their structures as novel diphenazine compounds, semi-synthesized some compounds thereof, confirmed the anticancer effect and physiological activity against neuroinflammation of these compounds, and then completed the present invention.

(Patent Document 001) Korean Patent Registration No. KR10-2120907

(Non-patent Document 001) *Mar. Drugs,* 2019, 17, 482.

DISCLOSURE

Technical Problem

The present invention has been made in an effort to provide a novel diphenazine compound, an enantiomer thereof, or a pharmaceutically acceptable salt thereof.

The present invention has also been made in an effort to provide a use of the novel diphenazine compound, an enantiomer thereof, or a pharmaceutically acceptable salt thereof.

The present invention has also been made in an effort to provide a method for preventing or treating cancer-related diseases including administering the novel diphenazine compound, an enantiomer thereof, or a pharmaceutically acceptable salt thereof to a subject in need thereof.

Technical Solution

Compound of Chemical Formula 1

An aspect of the present invention provides a novel diphenazine compound of Chemical Formula 1 below, an enantiomer thereof, or a pharmaceutically acceptable salt thereof.

[Chemical Formula 1]

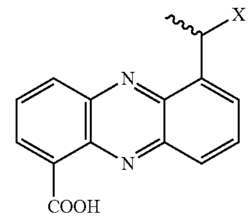

herein,

X is

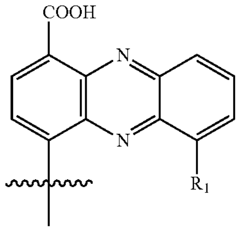
,

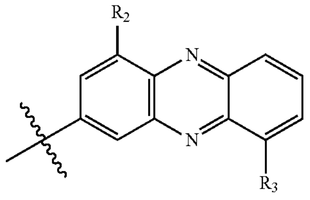
or

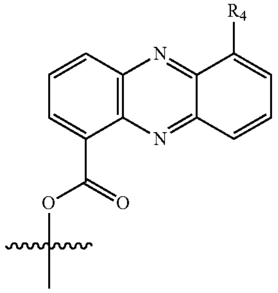
, $R_1$, $R_2$, $R_3$, and $R_4$ are each independently

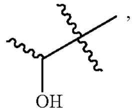 [SMILES: *C(C)O]

—OH, —COH, —COOH, —$COOCH_3$, or —$COCH_3$.

In the Chemical Formula of the present invention, when a symbol "" is used instead of a line representing a single bond, this means that the stereo arrangement of the stereogenic center has not been determined according to the stereo arrangement of the bond.

As an example, the symbol "" used in Chemical Formula 1 means that Chemical Formula 1 may have the structures of Chemical Formulas 1-1 and 1-2 below.

[Chemical Formula 1-1]

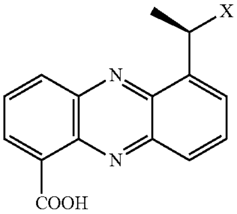

[Chemical Formula 1-2]

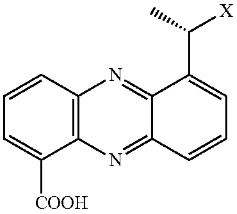

In addition, in the present invention, the symbol "

" indicates a point of attachment of a substituent to another group, and should not be confused with the symbol "", which is used instead of a line representing a single bond.

As an example,

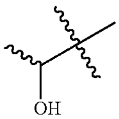

(—$CHCH_3OH$) of the present invention means that both

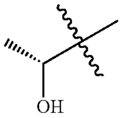

and

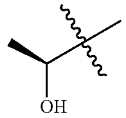

are possible.

In one embodiment, when the X is

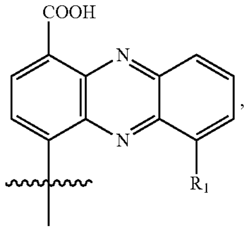

Chemical Formula 1 has the same structure as Chemical Formula 2 below.

[Chemical Formula 2]

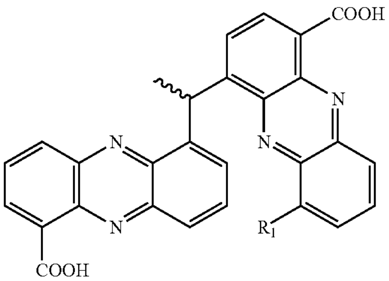

In Chemical Formula 2, $R_1$ is defined the same as Chemical Formula 1.

In one embodiment, when the X is

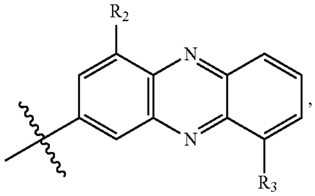

Chemical Formula 1 has the same structure as Chemical Formula 3 below.

[Chemical Formula 3]

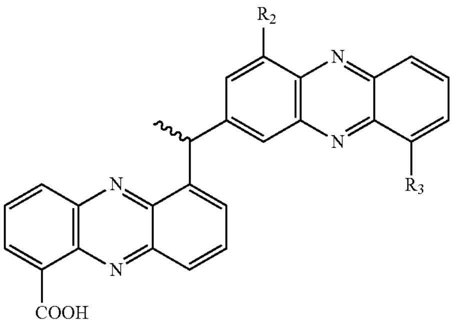

In Chemical Formula 3, $R_2$ and $R_5$ are defined the same as Chemical Formula 1.

In one embodiment, when the X is

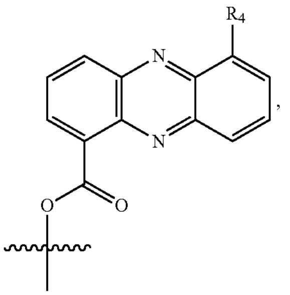

Chemical Formula 1 has the same structure as Chemical Formula 4 below.

[Chemical Formula 4]

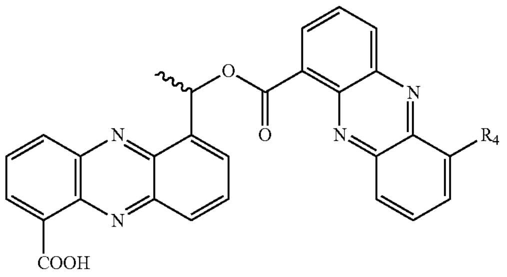

In Chemical Formula 4, Ra is defined the same as Chemical Formula 1.

In an embodiment of the present invention, when the X is

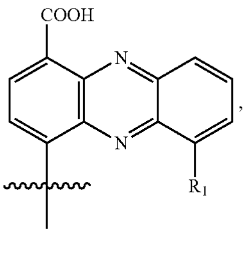

$R_1$ is

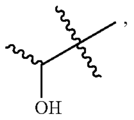 [SMILES: *C(C)O]

—COOH, or —$COCH_3$, but is not limited thereto.

In an embodiment of the present invention, when the X is

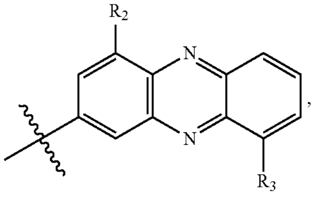

$R_1$ is

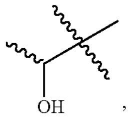 [SMILES: *C(C)O]

—COOH, or —$COCH_3$, but is not limited thereto.

In an embodiment of the present invention, when the X is

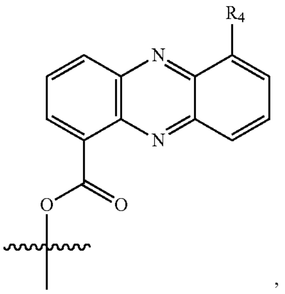

$R_1$ is

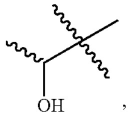 [SMILES: *C(C)O]

—COOH, or —$COCH_3$, but is not limited thereto.

According to an embodiment of the present invention, the compound of Chemical Formula 1 may be any one selected from the group consisting of the following compounds:

4-((R)-1-(6-carboxyphenazin-1-yl)ethyl)-6-((R)-1-hydroxyethyl)phenazine-1-carboxylic acid;

4-((S)-1-(6-carboxyphenazin-1-yl)ethyl)-6-((R)-1-hydroxyethyl)phenazine-1-carboxylic acid;

(R)-6-acetyl-4-(1-(6-carboxyphenazin-1-yl)ethyl) phenazine-1-carboxylic acid;

3-((S)-1-(6-carboxyphenazin-1-yl)ethyl)-6-((R)-1-hydroxyethyl)phenazine-1-carboxylic acid;

8-((R)-1-(6-carboxyphenazin-1-yl)ethyl)-6-((R)-1-hydroxyethyl)phenazine-1-carboxylic acid;

6-((R)-1-((6-((R)-1-hydroxyethyl)phenazine-1-carbonyl)oxy)ethyl)phenazine-1-carboxylic acid; and (R)-6-(1-((6-acetylphenazine-1-carbonyl)oxy)ethyl)phenazine-1-carboxylic acid.

The compound represented by Chemical Formula 1 of the present invention may contain one or more asymmetric carbons and thus, may exist as a racemate, a racemic mixture, a single enantiomer, a diastereomeric mixture, and an individual diastereomer.

These isomers are able to be separated by conventional techniques, and for example, the compound represented by Chemical Formula 1 is able to be separated by column chromatography, HPLC, or the like. Alternatively, each stereoisomer of the compound represented by Chemical Formula 1 may be stereospecifically synthesized using optically pure starting materials and/or reagents of known arrangement.

In addition, according to an embodiment of the present invention, the compound of Chemical Formula 1 may be any one selected from the group consisting of compounds of Table 1 below:

TABLE 1

| Examples | Structure |
| --- | --- |
| 1 | 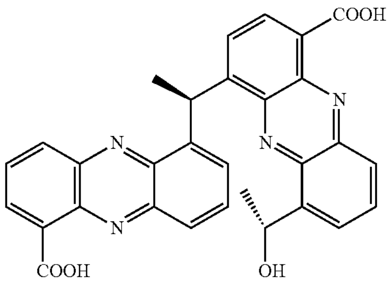 [SMILES: C[C@H](c1cccc2nc3c(C(=O)O)cccc3nc12)c1ccc(C(=O)O)c2nc3cccc([C@@H](C)O)c3nc12] |
| 2 | 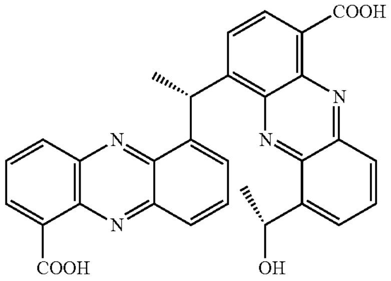 [SMILES: C[C@@H](c1cccc2nc3c(C(=O)O)cccc3nc12)c1ccc(C(=O)O)c2nc3cccc([C@@H](C)O)c3nc12] |
| 3 | 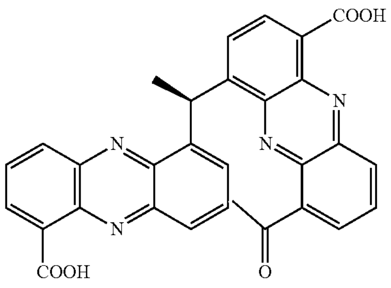 [SMILES: CC(=O)c1cccc2nc3c(C(=O)O)ccc([C@H](C)c4cccc5nc6c(C(=O)O)cccc6nc45)c3nc12] |

TABLE 1-continued

| Examples | Structure |
| --- | --- |
| 4 | 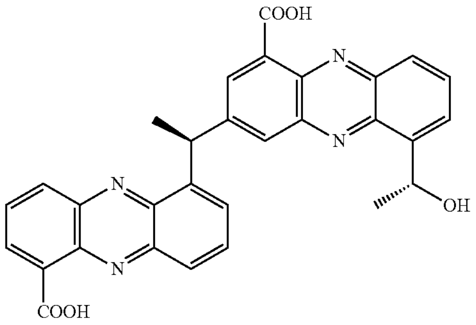 [SMILES: C[C@@H](c1cc(C(=O)O)c2nc3cccc([C@@H](C)O)c3nc2c1)c1cccc2nc3c(C(=O)O)cccc3nc12] |
| 5 | 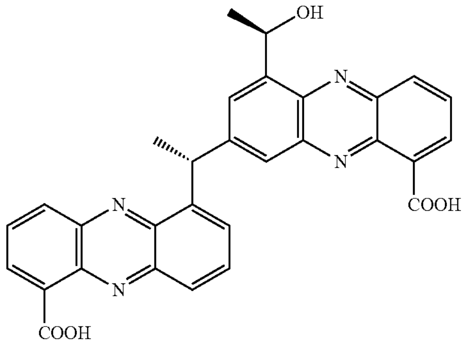 [SMILES: C[C@H](c1cc([C@@H](C)O)c2nc3cccc(C(=O)O)c3nc2c1)c1cccc2nc3c(C(=O)O)cccc3nc12] |
| 6 | 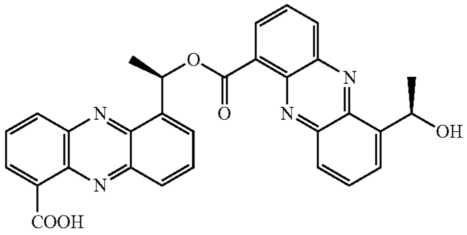 [SMILES: C[C@@H](O)c1cccc2nc3c(C(=O)O[C@H](C)c4cccc5nc6c(C(=O)O)cccc6nc45)cccc3nc12] |
| 7 | 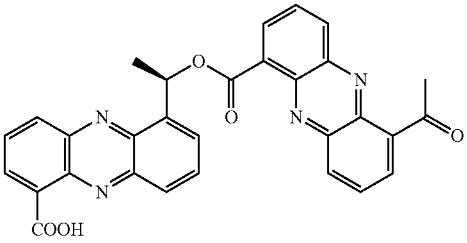 [SMILES: CC(=O)c1cccc2nc3c(C(=O)O[C@H](C)c4cccc5nc6c(C(=O)O)cccc6nc45)cccc3nc12] |

In the present invention, the pharmaceutically acceptable salt refers to salts commonly used in the pharmaceutical industry. For example, the pharmaceutically acceptable salt includes inorganic ion salts prepared from calcium, potassium, sodium, magnesium, etc.; inorganic acid salts prepared from hydrochloric acid, nitric acid, phosphoric acid, bromic acid, iodic acid, perchloric acid, sulfuric acid, etc.; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts prepared from methanesulfonic acid, ethanesulfonic acid, benzenesulfonic acid, p-toluenesulfonic acid, naphthalenesulfonic acid, etc.;

amino acid salts prepared from glycine, arginine, lysine, etc.; and amine salts prepared from trimethylamine, triethylamine, ammonia, pyridine, picoline, etc. However, the types of salts meant in the present invention are not limited to these listed salts.

Manufacturing Method of the Compound of Chemical Formula 1

The present invention provides a method for manufacturing the compound of Chemical Formula 1, an enantiomer thereof or a pharmaceutically acceptable salt thereof including isolating a diphenazine compound represented by Chemical Formula 1 below, an enantiomer thereof or a pharmaceutically acceptable salt thereof from the *Cystobasidium laryngis* IV17-028 KCTC 13720BP strain or a culture medium thereof.

In the present invention, the culture medium for the *Cystobasidium laryngis* IV17-028 KCTC 13720BP strain may be obtained by culturing the strain in a liquid medium or solid medium. The medium may include, as a non-limiting example, glucose, starch syrup, dextrin, starch, molasses, animal oil or vegetable oil as a carbon source. In addition, the medium may include, as a non-limiting example, wheat bran, soybean meal, wheat, malt, cottonseed meal, fish meal, corn steep liquor, broth, yeast extract, ammonium sulfate, sodium nitrate, or urea as a nitrogen source. In addition, the medium may contain salt, potassium, magnesium, cobalt, chlorine, phosphoric acid, sulfuric acid, or other inorganic salts that promote ion production, if necessary. The strain may be cultured while shaking or standing, and the culture temperature may be about 20° C. to about 37° C., preferably about 25° C. to about 30° C.

The compound of Chemical Formula 1 may be obtained by solvent extraction, concentration, and column chromatography for the strain or the culture medium thereof. The concentration may be performed by adding a solvent to the strain or the culture medium thereof and evaporating an extract under reduced pressure. As the solvent, ethyl acetate, chloroform, methylene chloride, and lower alcohols having 1 to 4 carbon atoms may be used, and preferably, ethyl acetate, chloroform, methylene chloride, and methanol may be used. The chromatography may be column chromatography, plate chromatography, paper chromatography, or thin-layer chromatography, depending on the form of a stationary phase. Alternatively, the chromatography may be high-performance liquid chromatography (HPLC) or gas chromatography depending on the physical characteristics of a mobile phase.

According to an embodiment of the present invention, the ethyl acetate extract of the strain or the culture medium thereof may be fractionated by solvent-solvent extraction, silica and reversed-phase flash column chromatography, and then purified by HPLC to obtain a compound of Chemical Formula 1.

Accordingly, the present invention provides a method for manufacturing a compound of Chemical Formula 1, an enantiomer thereof or a pharmaceutically acceptable salt thereof including (a) culturing the *Cystobasidium laryngis* IV17-028 KCTC 13720BP strain;

(b) extracting the culture medium of step (a) with ethyl acetate;

(c) extracting the extract of step (b) with chloroform;

(d) eluting the chloroform extract of step (c) stepwise with $CH_2Cl_2$/MeOH, in which the stepwise elution is performed with a solvent having a v/v ratio of $CH_2Cl_2$ and MeOH of 10:0, 20:1, 10:1, 5:1, and 1:1;

(e) eluting a result product eluted in step (d) stepwise with MeOH/$H_2O$, in which the stepwise elution is performed with a solvent having a v/v ratio of MeOH and $H_2O$ of 1:4, 2:3, 3:2, 4:1, or 5:0; and (f) eluting the eluted fraction with 80% methanol and purifying the isolated compound of Chemical Formula 1.

Use of the Compound of Chemical Formula 1

The present invention provides a use of a diphenazine compound represented by Chemical Formula 1 below, an enantiomer thereof, or a pharmaceutically acceptable salt thereof.

[Chemical Formula 1]

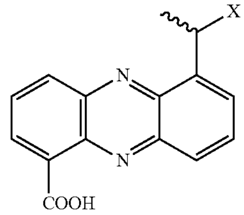

herein,

X is

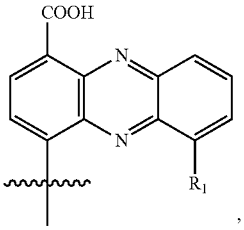

,

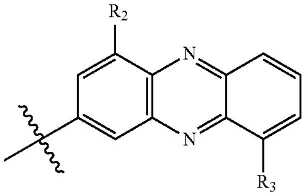

or

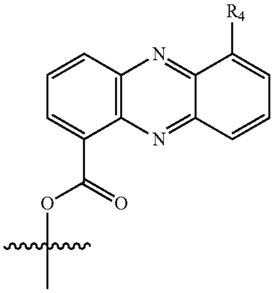

, $R_1$, $R_2$, $R_3$, and $R_4$ are each independently

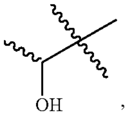 [SMILES: *C(C)O]

,

—OH, —COH, —COOH, —$COOCH_3$, or —$COCH_3$.

The present invention provides a pharmaceutical composition including the diphenazine compound of Chemical Formula 1, an enantiomer thereof, or a pharmaceutically acceptable salt thereof as an active ingredient.

The present invention provides a pharmaceutical composition for preventing or treating cancer including the diphenazine compound of Chemical Formula 1, an enantiomer thereof, or a pharmaceutically acceptable salt thereof as an active ingredient.

In the present invention, non-limiting examples of cancer may include pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian cancer, ovarian epithelial cancer, ovarian germ cell cancer, male breast cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, diffuse large B-cell lymphoma, ampullar of vater cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, childhood brain cancer, childhood lymphoma, childhood leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, stomach cancer, gastric carcinoid, gastrointestinal cancer, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, mesothelioma, rectal cancer, rectal carcinoid, vaginal cancer, spinal cord cancer, acoustic neuroma, pancreatic cancer, salivary gland cancer, Kaposi's sarcoma, Paget's disease, tonsillar cancer, squamous cell carcinoma, lung adenocarcinoma, lung cancer, lung squamous cell carcinoma, skin cancer, anal cancer, rhabdomyosarcoma, laryngeal cancer, pleural cancer, or thymic cancer.

The present invention provides a pharmaceutical composition for preventing or treating neuroinflammatory diseases including the diphenazine compound of Chemical Formula 1, an enantiomer thereof, or a pharmaceutically acceptable salt thereof as an active ingredient.

In the present invention, non-limiting examples of neuroinflammatory diseases may include brain inflammatory diseases, multiple sclerosis, depression, stroke, Alzheimer's disease, Parkinson's disease, Lou Gehrig's disease, Huntington's disease, Creutzfeldt-Jakob disease, post-traumatic stress disorder, schizophrenia, amyotrophic lateral sclerosis, and the like.

The pharmaceutical composition of the present invention may further include at least one pharmaceutically acceptable carrier in addition to the diphenazine compound of Chemical Formula 1, the enantiomer thereof, or the pharmaceutically acceptable salt thereof for administration. The pharmaceutically acceptable carrier may be used by mixing saline, sterile water, Ringer's solution, buffered saline, a dextrose solution, a maltodextrin solution, glycerol, ethanol, and at least one of these ingredients, and if necessary, other conventional additives such as antioxidants, buffers, bacteriostats, etc. may be added. In addition, the pharmaceutical composition may be prepared in injectable formulations such as aqueous solutions, suspensions, and emulsions, pills, capsules, granules, or tablets by further adding a diluent, a dispersant, a surfactant, a binder, and a lubricant. Accordingly, the pharmaceutical composition of the present invention may be patches, liquids, pills, capsules, granules, tablets, suppositories or the like. These formulations may be prepared by conventional methods used for formulation in the art or by methods disclosed in Remington's Pharmaceutical Science (latest edition), Mack Publishing Company, Easton PA, and may be prepared into various formulations according to each disease or an ingredient.

The pharmaceutical composition of the present invention may be administered orally or parenterally (e.g., intravenously, subcutaneously, intraperitoneally, or topically) according to a desired method, and the range of the dose may vary depending on the body weight, age, sex, and health condition of a patient, a diet, an administration time, an administration method, an excretion rate, the type and severity of a disease, and the like. The daily dose of the compound of Chemical Formula 1 of the present invention is about 0.01 to 1,000 mg/kg, preferably 0.1 to 100 mg/kg, and may be administered once or several times a day.

The pharmaceutical composition of the present invention may further include at least one active ingredient having the same or similar efficacy in addition to the diphenazine compound of Chemical Formula 1, the enantiomer thereof, or the pharmaceutically acceptable salt thereof.

The present invention provides a method for treating or preventing cancer, including administering the diphenazine compound of Chemical Formula 1, the enantiomer thereof, or the pharmaceutically acceptable salt thereof in a therapeutically effective amount to mammals, including humans.

The present invention provides a method for treating or preventing neuroinflammatory diseases, including administering the diphenazine compound of Chemical Formula 1, the enantiomer thereof, or the pharmaceutically acceptable salt thereof in a therapeutically effective amount to mammals, including humans.

The term therapeutically effective amount used in the present invention refers to an amount of the diphenazine compound of Chemical Formula 1, the enantiomer thereof, or the pharmaceutically acceptable salt thereof effective in preventing or treating cancer or neuroinflammatory diseases.

The treating method of the present invention includes not only treating the disease itself before the onset of symptoms, but also inhibiting or avoiding symptoms thereof, by administering the compound of Chemical Formula 1. In the management of the diseases, a prophylactic or therapeutic dose of a specific active ingredient will vary depending on the nature and severity of the disease or condition, and a route by which the active ingredient is administered. The dose and the dose frequency will vary according to the age, body weight and response of an individual patient. A suitable dosage regimen may be easily selected by those skilled in the art who certainly consider these factors. In addition, the treating method of the present invention may further include administering a therapeutically effective dose of an additional active agent to help in treating the diseases together with the compound of Chemical Formula 1, and the additional active agent may exhibit a synergistic or auxiliary effect together with the compound of Chemical Formula 1.

The present invention provides a food composition for preventing or improving cancer including the diphenazine compound of Chemical Formula 1, or a pharmaceutically acceptable salt thereof as an active ingredient.

The present invention provides a food composition for preventing or improving neuroinflammatory diseases including the diphenazine compound of Chemical Formula 1, or a pharmaceutically acceptable salt thereof as an active ingredient.

The food composition of the present invention may be used as a health functional food. The "health functional food" refers to food produced and processed using raw materials or ingredients with functionality, which are useful for the human body according to the Art on Health Functional Foods No. 6727, and the "functionality" means intake for adjusting nutrients for the structures and functions of the human body or obtaining an useful effect on health applications such as physiological actions.

The food composition of the present invention may include conventional food additives, and the suitability as the "food additive" is determined by the specifications and standards for the corresponding item in accordance with the general rules of the Food Additive Codex, general test methods, and the like approved by the Food and Drug Administration, unless otherwise specified.

The food composition of the present invention may include the compound of Chemical Formula 1 in an amount of 0.01 to 95 wt %, preferably 1 to 80 wt %, based on the total weight of the composition, for the purpose of preventing and/or improving cancer and/or neuroinflammatory diseases. In addition, the food composition may be produced and processed in the form of tablets, capsules, powders, granules, liquids, pills, beverages, and the like, for the purpose of preventing and/or improving cancer-related diseases and/or neuroinflammatory diseases.

In addition, the present invention provides a use of the diphenazine compound of Chemical Formula 1, or a pharmaceutically acceptable salt thereof, for the preparation of a drug for the treatment of cancer and/or neuroinflammatory diseases. For the preparation of the drug, the compound of Chemical Formula 1 may be mixed with acceptable adjuvants, diluents, carriers, and the like, and may be prepared as a complex preparation together with other active agents to have a synergistic action of the active ingredients.

Matters mentioned in the composition, the use, and the treatment method of the present invention are applied equally unless they contradict each other.

The present invention provides a method for preventing or treating cancer-related diseases including administering the diphenazine compound of Chemical Formula 1, or a pharmaceutically acceptable salt thereof to a subject in need thereof. At this time, the cancer-related disease is not particularly limited thereto, but may be at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian cancer, ovarian epithelial cancer, ovarian germ cell cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, diffuse large B-cell lymphoma, ampullar of vater cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, childhood brain cancer, childhood lymphoma, childhood leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, stomach cancer, gastric carcinoid, gastrointestinal cancer, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, mesothelioma, rectal cancer, rectal carcinoid, vaginal cancer, spinal cord cancer, acoustic neuroma, pancreatic cancer, salivary gland cancer, Kaposi's sarcoma, Paget's disease, tonsillar cancer, squamous cell carcinoma, lung adenocarcinoma, lung cancer, lung squamous cell carcinoma, skin cancer, anal cancer, rhabdomyosarcoma, laryngeal cancer, pleural cancer, and thymic cancer.

Advantageous Effects

According to the present invention, the novel diphenazine compound, the enantiomer thereof, or the pharmaceutically acceptable salt thereof has an excellent prophylactic or therapeutic effect against the above-mentioned types of cancer by selectively and excellently exhibiting cytotoxicity against cancer cell lines, and has an excellent prophylactic or therapeutic effect against the above-mentioned types of neuroinflammatory diseases by exhibiting the neuroinflammatory disease inhibitory activity in LPS-induced microglia.

DESCRIPTION OF DRAWINGS

FIG. 3 illustrates $\Delta\delta_H$ values of MTPA esters of Compounds 1, 2, 4, 5, and 6 by ($\delta_{S\text{-}ester}$-$\delta_{R\text{-}ester}$) ppm.

FIG. 4 illustrates experimental and calculated ECD spectra for Compounds 1 and 2.

FIG. 5 illustrates stereostructures of Compounds 1 and 2.

FIG. 6 illustrates experimental and calculated ECD spectra for Compound 4.

FIG. 7 illustrates experimental and calculated ECD spectra for Compound 5.

FIG. 11 illustrates chemical structures of Compounds 1 to 9 of the present invention.

MODES FOR THE INVENTION

Figure 1:
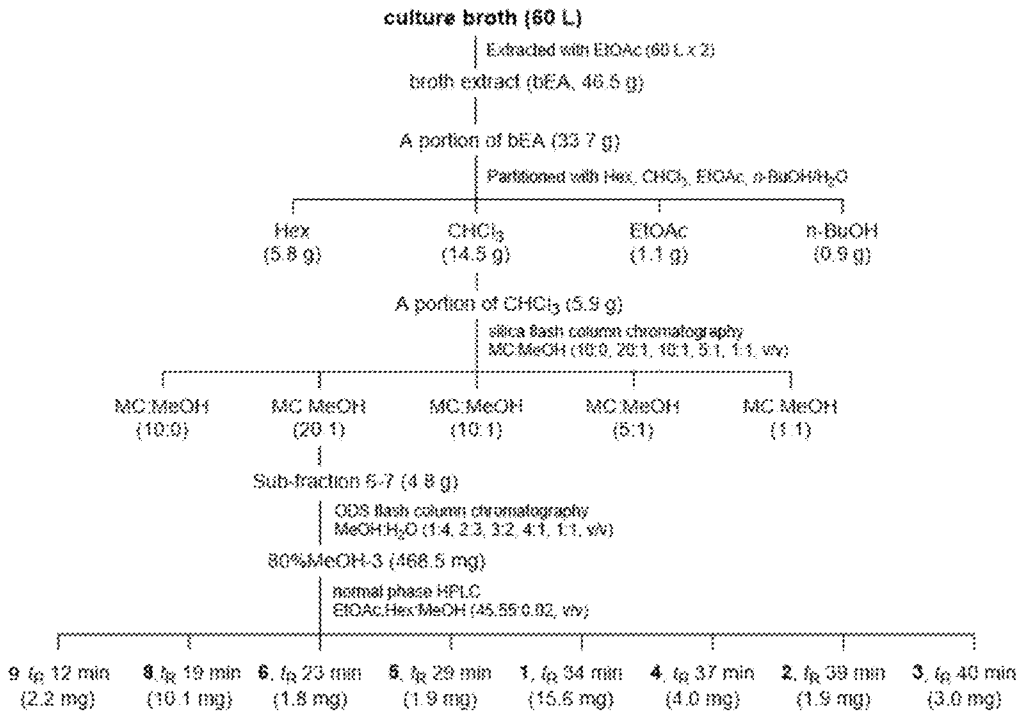
FIG. 1 illustrates a process of fractionating Compounds 1 to 6, Compound 8, and Compound 9.

Hereinafter, Examples of the present invention will be described in detail so as to easily implement those skilled in the art. However, the present invention may be embodied in many different forms and are limited to examples described herein.

Example 1. Production of Diphenazine Compound

Experimental Devices

Specific optical rotation was measured using an Autopol III S2 polarimeter from Rudolph analytical. A CD spectrum was measured using a J-1500 polarimeter from JASCO located at the Center for Research Facilities, Changwon National University in Changwon, Korea. A UV spectrum was obtained using a UV-1650PC spectrophotometer from Shimadzu, and an IR spectrum was obtained using a FT/IR-4100 spectrophotometer from JASCO. An NMR spectrum was obtained using a 3 mm probe by measuring $^1$H at 600 MHz and $^{13}$C at 150 Hz with an AVANCE III 600 spectrometer from Bruker. Chemical shift values were based on the solvent peaks ($\delta_H$ 7.24, $\delta_H$ 77.23) of $CDCl_3$. ESIMS data were obtained using a 6100 single quadrupole mass spectrometer from Agilent, and HR-ESIMS data were obtained using a SYNPT G2 Q-TOF mass spectrometer from Waters at the Korea Basic Science Institute (KBSI) in Cheongju, Korea. High-performance liquid chromatography (HPLC) consisting of a binary pump from PrimeLine, a RI-101 refractive index detector from Shodex, and a S3210 variable UV detector was used. HPLC columns were used with YMC-pack Silica (250 mm×10 mm, 5 μm), and YMC-Triart $C_{18}$ (250 mm×10 mm, 5 μm and 250 mm×4.6 mm, 5 μm). Silica gel 60 (Merck, 230-400 mesh) and reversed-phase silica gel (YMC-Gel ODS-A, 12 nm, S-75 μm) were used as fillers for open column chromatography. Mass culture was performed using a 100 L fermenter from Fermentec. All solvents were used with HPLC grade or distilled solvents.

Isolation and Mass Culture of the Strain IV17-028

*Cystobasidium laryngis* IV17-028 (GenBank accession number: MK131277) was isolated from deep-sea sediment collected at a depth of 4,317 m in the Indian Ocean.

The strain *Cystobasidium laryngis* IV17-028 was cultured on a Bennett (BN) agar medium at 28° C. for 7 days, and thereafter, the strain was inoculated into a 2 L flask containing 600 mL of a BN broth (containing 10 g glucose, 1 g yeast extract, 2 g tryptone, 1 g beef extract, 5 g glycerol, and 32 g marine salt in 1 L distilled water) and cultured at 28° C. for 5 days while stirring at 140 rpm. The culture medium was inoculated into a 100 L fermenter containing 60 L BN broth, and mass-cultured for 10 days under conditions of 28° C., 50 rpm, and 20 LPM.

The strain *Cystobasidium laryngis* IV17-028 was deposited on Nov. 20, 2018 and was assigned the deposit number KCTC 13720BP.

Isolation of the Compounds

The 60 L mass-cultured medium was extracted twice with the same amount of ethyl acetate (EtOAc), for a total of 120 L. The EtOAc extract was concentrated to obtain about 46 g of a crude extract. At this time, 33.7 g of the crude extract was sequentially fractionated with 1 L of water, n-hexane, chloroform, ethyl acetate (EtOAc), and n-butanol (n-BuOH), and the fractions were obtained at 5.8, 14.5, 1.1, and 0.9 g, respectively. 5.8 g of the chloroform concentrate was eluted stepwise with an organic solvent mixed at the ratios of methylene chloride ($CH_2Cl_2$): methanol (MeOH) (v/v, 10:0, 20:1, 10:1, 5:1, and 1:1) using silica flash column chromatography. The $CH_2Cl_2$/MeOH (20:1) fraction were divided into a total of nine. Among these, 4.8 of subfractions 6-7 were eluted stepwise with an organic solvent mixed at a ratio of methanol:water (v/v, 1:4, 2:3, 3:2, 4:1, and 5:0) using reversed-phase flash column chromatography, and each fraction was divided into three. 468.5 mg of the third 80% methanol fraction was subjected to normal phase HPLC (YMC-Pack SIL 250 mm×10 mm, 5 μm; EtOAc/Hex/MeOH (v/v, 45:55:0.02); flow rate: 2.0 mL/min; detector: RI) to separate and purify 6 compounds (1: 15.6 mg, $t_R$ 34 min, 2: 1.9 mg, $t_R$ 39 min, 3: 3.0 mg, $t_R$ 40 min, 4: 4.0 mg, $t_R$ 37 min, 5: 1.9 mg, (R 29 min, 6: 1.8 mg, (R 23 min) (FIG. 1).

1. 4-((R)-1-(6-Carboxyphenazin-1-Yl)Ethyl)-6-((R)-1-Hydroxyethyl)Phenazine-1-Carboxylic Acid (Phenazostatin E)

Light green, amorphous;

$$[\alpha]_D^{25} - 167(c\ 0.1,\ CHCl_3);$$

UV ($CHCl_3$) $\lambda_{max}$ (log ε) 371 (1.45), 253 (2.06) nm; IR ($CHCl_3$) $\gamma_{max}$ 3360, 2922, 1728, 1456, 1219, 770 $cm^{-1}$; $^1$H and $^{13}$C NMR data, Table 2; HR-ESIMS m/z 541.1487 $[M+Na]^+$ (calcd for $C_{30}H_{22}N_4O_5Na$, 541.1488).

2. 4-((S)-1-(6-Carboxyphenazin-1-Yl)Ethyl)-6-((R)-1-Hydroxyethyl)Phenazine-1-Carboxylic Acid (Phenazostatin F)

Light green, amorphous;

$$[\alpha]_D^{25} + 88\ (c\ 0.1,\ CHCl_3);$$

UV ($CHCl_3$) $\lambda_{max}$ (log ε) 371 (1.14), 253 (1.74) nm; IR ($CHCl_3$) $\gamma_{max}$ 3728, 3629, 3360, 2922, 1727, 1452, 1218, 770 $cm^{-1}$; $^1$H and $^{13}$C NMR data, Table 2; HR-ESIMS m/z 541.1489 $[M+Na]^+$ (calcd for $C_{30}H_{22}N_4O_5Na$, 541.1488).

3. (R)-6-Acetyl-4-(1-(6-Carboxyphenazin-1-Yl) Ethyl)Phenazine-1-Carboxylic Acid (Phenazostatin G)

Light green, amorphous;

$$[\alpha]_D^{25} - 33\ (c\ 0.1,\ CHCl_3);$$

UV ($CHCl_3$) $\lambda_{max}$ (log ε) 372 (1.62), 255 (2.21) nm; IR ($CHCl_3$) $\gamma_{max}$ 2925, 2855, 2703, 1732, 1459, 1261, 760 $cm^{-1}$; $^1$H and $^{13}$C NMR data, Table 2; HR-ESIMS m/z 539.1331 $[M+Na]^+$ (calcd for $C_{30}H_{20}N_4O_5Na$, 539.1331).

4. 3-((S)-1-(6-Carboxyphenazin-1-Yl)Ethyl)-6-((R)-1-Hydroxyethyl)Phenazine-1-Carboxylic Acid (Phenazostatin H)

Light green, amorphous;

$$[\alpha]_D^{25} - 137\ (c\ 0.1,\ CHCl_3);$$

UV ($CHCl_3$) $\lambda_{max}$ (log ε) 372 (1.61), 259 (2.19) nm; IR ($CHCl_3$) $\gamma_{max}$ 3452, 2957, 2689, 1721, 1617, 1459, 1261, 773 $cm^{-1}$; $^1$H and $^{13}$C NMR data, Table 3; HR-ESIMS m/z 541.1486 $[M+Na]^+$ (calcd for $C_{30}H_{22}N_4O_5Na$, 541.1488).

5. 8-((R)-1-(6-Carboxyphenazin-1-Yl)Ethyl)-6-((R)-1-Hydroxyethyl)Phenazine-1-Carboxylic Acid (Phenazostatin I)

Light green, amorphous;

$$[\alpha]_D^{25} - 33\ (c\ 0.1,\ CHCl_3);$$

UV ($CHCl_3$) $\lambda_{max}$ (log ε) 371 (0.52), 253 (1.07) nm; IR ($CHCl_3$) $\gamma_{max}$ 3356, 3190, 2922, 2855, 1657, 1458, 1218, 770 $cm^{-1}$; $^1H$ and $^{13}C$ NMR data, Table 3; HR-ESIMS m/z 541.1487 $[M+Na]^+$ (calcd for $C_{30}H_{22}N_4O_5Na$, 541.1488).

6. 6-((R)-1-((6-((R)-1-Hydroxyethyl)Phenazine-1-Carbonyl)Oxy)Ethyl)Phenazine-1-Carboxylic Acid (Phenazostatin J)

Light green, amorphous;

$[\alpha]_D^{25}$ −27 (*c* 0.1, $CHCl_3$);

UV ($CHCl_3$) $\lambda_{max}$ (log ε) 371 (1.53), 253 (2.14) nm; IR ($CHCl_3$) $\gamma_{max}$ 3353, 2925, 2855, 1731, 1462, 1261, 773 $cm^{-1}$; $^1H$ and $^{13}C$ NMR data, Table 4; HR-ESIMS m/z 541.1491 $[M+Na]^+$ (calcd for $C_{30}H_{22}N_4O_5Na$, 541.1488).

The $^1H$ NMR (600 MHz) and $^{13}C$ NMR (150 MHz) results in $CDCl_3$ for Compounds 1 to 3 were shown in Table 2 below, and the $^1H$ NMR (600 MHz) and $^{13}C$ NMR (150 MHz) results in $CDCl_3$ for Compounds 4 to 6 were shown in Table 3 below.

TABLE 2

| | Phenazostatin E (1) | | Phenazostatin F (2) | | Phenazostatin G (3) | |
|---|---|---|---|---|---|---|
| position | $\delta_C$, type | $\delta_H$, mult. (J in Hz) | $\delta_C$, type | $\delta_H$, mult. (J in Hz) | $\delta_C$, type | $\delta_H$, mult. (J in Hz) |
| 1 | 125.0, C | | 125.1[a], C | | 125.1, C | |
| 2 | 137.7, CH | 8.93, dd (7.1, 1.4) | 137.8, CH | 8.96, dd (7.1, 1.5) | 138.2, CH | 8.93, overlapped |
| 3 | 130.5, CH | 7.95, dd (8.7, 7.1) | 130.5, CH | 7.98, dd (8.6, 7.1) | 130.4, CH | 7.91, overlapped |
| 4 | 135.6, CH | 8.33, dd (8.7, 1.4) | 135.7, CH | 8.43, dd (8.6, 1.5) | 135.3, CH | 8.15, overlapped |
| 4a | 142.9, C | | 143.1[a], C | | 140.3[a], C | |
| 5a | 142.3, C | | 142.2[a], C | | 142.6[a], C | |
| 6 | 145.8, C | | 145.7[a], C | | 145.2[a], C | |
| 7 | 128.8, CH | 7.67, d (7.0) | 128.9, CH | 7.63, d (6.9) | 128.9, CH | 7.70, d (7.0) |
| 8 | 133.2, CH | 7.86, dd (8.7, 7.0) | 133.3, CH | 7.85, dd (8.1, 6.9) | 133.2, CH | 7.89, overlapped |
| 9 | 126.9, CH | 8.13, dd (8.7, 0.7) | 126.9, CH | 8.14, dd (8.1, 0.8) | 127.1, CH | 8.17, overlapped |
| 9a | 140.5, C | | 140.1[a], C | | 143.5[a], C | |
| 10a | 140.2, C | | 140.2[a], C | | 140.6[a], C | |
| 11 | 166.0, C | | 166.1[a], C | | 166.1[a], C | |
| 12 | 34.1, CH | 7.07, q (14.0, 7.0) | 34.0, CH | 7.09, q (14.4, 7.4) | 34.5, CH | 7.04, q (14.3, 7.2) |
| 13 | 21.4, $CH_3$ | 2.00, d (7.0) | 21.4, $CH_3$ | 2.00, d (7.4) | 21.2, $CH_3$ | 2.02, d (7.2) |
| 1' | 123.6, C | | 123.6[a], C | | 123.6[a], C | |
| 2' | 137.5, CH | 8.95, d (7.4) | 137.5[a], CH | 8.97, d (7.4) | 137.7, CH | 8.93, overlapped |
| 3' | 128.6, CH | 8.02, d (7.4) | 128.5, CH | 8.07, d (7.4) | 129.0, CH | 7.92, overlapped |
| 4' | 150.9, C | | 150.8[a], C | | 152.0[a], C | |
| 4a' | 140.2, C | | 140.4[a], C | | 140.7[a], C | |
| 5a' | 141.3, C | | 141.6[a], C | | 141.0[a], C | |
| 6' | 143.7, C | | 143.8[a], C | | 139.3[a], C | |
| 7' | 127.9, CH | 7.77, d (6.8) | 127.9, CH | 7.75, d (6.9) | 132.2, CH | 8.17, overlapped |
| 8' | 133.4, CH | 7.91, dd (9.0, 6.8) | 133.4, CH | 7.90, dd (8.6, 6.9) | 132.6, CH | 8.03, dd (8.7, 7.1) |
| 9' | 127.2, CH | 8.15, dd (9.0, 1.4) | 127.1, CH | 8.13, d (8.6) | 131.5, CH | 8.41, d (8.7) |
| 9a' | 140.4, C | | 140.5[a], C | | 140.8[a], C | |
| 10a' | 140.0, C | | 139.8[a], C | | 140.5[a], C | |
| 11' | 166.1, C | | 166.0[a], C | | 165.8[a], C | |
| 12' | 67.8, CH | 5.24, q (13.7, 6.8) | 67.9, CH | 4.95, p (13.1, 6.6, 6.5) | 200.3[a], C | |
| 13' | 22.9, $CH_3$ | 1.12, d (6.8) | 23.6, $CH_3$ | 1.13, d (6.6) | 32.7, $CH_3$ | 2.67, s |

[a]Chemical shift value was obtained from the HMBC spectrum.

TABLE 3

| | Phenazostatin H (4) | | Phenazostatin I (5) | | Phenazostatin J (6) | |
|---|---|---|---|---|---|---|
| position | $\delta_C$, type | $\delta_H$, mult. (J in Hz) | $\delta_C$, type | $\delta_H$, mult. (J in Hz) | $\delta_C$, type | $\delta_H$, mult. (J in Hz) |
| 1 | 125.1[a], C | | 125.5[a], C | | 125.1[a], C | |
| 2 | 137.8, CH | 8.93, d (6.8) | 137.7, CH | 8.93, dd (7.1, 1.4) | 137.8, CH | 8.99, dd (7.0. 1.3) |
| 3 | 130.6, CH | 7.99, t (8.4) | 130.2, CH | 7.93, dd (8.7, 7.1) | 132.1[a], CH | 8.05, overlapped |
| 4 | 135.6, CH | 8.54, d (8.1) | 135.6, CH | 8.33, dd (8.7, 1.4) | 135.7, CH | 8.62, dd (8.6, 1.3) |
| 4a | 142.4, C | | 142.9[a], C | | 140.0[a], C | |
| 5a | 142.2, C | | 143.0[a], C | | 141.6[a], C | |
| 6 | 144.2[a], C | | 144.9[a], C | | 141.7[a], C | |
| 7 | 129.1, CH | 7.95, d (6.8) | 128.5[a], CH | 7.63, dd (6.9, 0.9) | 127.6, CH | 8.54, d (7.0) |
| 8 | 132.9, CH | 7.91, t (6.9) | 133.0, CH | 7.84, dd (8.7, 6.9) | 132.0[a], CH | 8.05, overlapped |
| 9 | 127.0, CH | 8.12, d (8.3) | 126.9, CH | 8.14, dd (8.7, 0.9) | 126.9[a], CH | 8.25, d (8.7) |
| 9a | 140.3[a], C | | 140.2[a], C | | 143.0[a], C | |
| 10a | 140.2, C | | 137.0[a], C | | 139.2[a], C | |
| 11 | 166.0, C | | 165.7[a], C | | 166.2[a], C | |
| 12 | 39.7, CH | 5.97, q (14.3, 7.1) | 33.8, CH | 6.78, q (13.8, 7.0) | 70.0, CH | 7.65, q (13.2, 6.6) |
| 13 | 21.0, $CH_3$ | 2.06, d (7.1) | 21.6, $CH_3$ | 2.01, d (7.0) | 22.9. $CH_3$ | 1.98 d (6.6) |
| 1' | 124.6[a], C | | 124.9[a], C | | 131.6[a], C | |
| 2' | 140.0, CH | 9.16, s | 137.6, CH | 8.90, dd (7.1, 1.4) | 132.6, CH | 8.33, dd (6.9, 1.3) |

TABLE 3-continued

| | Phenazostatin H (4) | | Phenazostatin I (5) | | Phenazostatin J (6) | |
|---|---|---|---|---|---|---|
| position | $\delta_C$, type | $\delta_H$, mult. (J in Hz) | $\delta_C$, type | $\delta_H$, mult. (J in Hz) | $\delta_C$, type | $\delta_H$, mult. (J in Hz) |
| 3' | 149.6[a], C | | 130.7[a], CH | 8.02, dd (6.6, 7.1) | 129.6, CH | 7.90, dd (8.7, 6.9) |
| 4' | 131.7, CH | 8.41, s | 134.9[a], CH | 8.51, dd (8.7, 1.5) | 133.3, CH | 8.39, dd (8.7, 1.3) |
| 4a' | 140.0, C | | 141.6[a], C | | 140.8[a], C | |
| 5a' | 142.6[a], C | | 140.5[a], C | | 141.8[a], C | |
| 6' | 143.5, C | | 142.2[a], C | | 142.7[a], C | |
| 7' | 127.7, CH | 7.87, d (7.0) | 131.4, CH | 7.90, s | 128.0, CH | 7.80, d (6.6) |
| 8' | 132.9, CH | 8.03, t (7.0) | 143.6[a], C | | 131.2, CH | 7.85, dd (8.7, 6.6) |
| 9' | 127.3, CH | 8.20, d (8.6) | 127.6[a], CH | 7.90, s | 129.4, CH | 8.17, dd (8.7, 1.3) |
| 9a' | 140.6[a], C | | | | 143.3[a], C | |
| 10a' | 139.2[a], C | | 138.1[a], C | | 141.0[a], C | |
| 11' | 166.2[a], C | | 165.9[a], C | | 165.8[a], C | |
| 12' | 68.6, CH | 5.74, q (13.2, 6.6) | 67.7, CH | 5.82, m | 69.1, CH | 5.72, br |
| 13' | 24.1, $CH_3$ | 1.77, d (6.6) | 23.7, $CH_3$ | 1.79, d (6.5) | 23.9, $CH_3$ | 1.81, d (6.6) |

[a]Chemical shift value was obtained from the HMBC spectrum.

MTPA Esterification of Compounds 1, 2, and 4 to 6

Compounds 1, 2, and 4-6 were MTPA-esterified using a modified Mosher's method to confirm the absolute structures of Compound 1, 2, and 4-6.

Compound 1 (by 0.2 mg, 0.4 μmol) was added to two 350 μL tubes and dried with $N_2$ gas. A small amount of 4-dimethylaminopyridine (DMAP) and a stirring magnet were added, and then vacuum dried for 16 hours. 80 μL of anhydrous pyridine was added and then stirred at room temperature for 5 minutes. Then, 3 μL of S- or R-MTPA-Cl was added to each tube and stirred at room temperature for 16 hours. The reactant was concentrated at 40° C. with $N_2$ gas. The reactant was dissolved in MC and washed with 1 N hydrogen chloride (HCl), saturated sodium bicarbonate ($NaHCO_3$) solution, and brine. The organic layer was dehydrated with anhydrous magnesium sulfate ($MgSO_4$), filtered, and concentrated under reduced pressure. The remaining Compounds 2 and 4-6 were also S- or R-MTPA esterified using the same method. The chemical shift values around the stereocenter of the MTPA esterified compounds were confirmed through $^1$H and COSY spectrum analysis. (FIG. 3)

S-MTPA ester of Compound 1 (1a): $^1$H NMR (600 MHz, $CDCl_3$) $\delta_H$ 9.0586 (d, J=7.5 Hz, H-2'), 8.2041 (d, J=7.5 Hz, H-3'), 8.1139 (d, J=8.7 Hz, H-9'), 7.7693 (t, J=8.7 Hz, H-8'), 6.1745 (q, J=6.8 Hz, H-12'), 1.4882 (d, J=6.6 Hz, H-13'); ESIMS m/z $[M-H]^-$ 733.0.

R-MPTA ester of Compound 1 (1b): $^1$H NMR (600 MHz, $CDCl_3$) δ H 9.0679 (d, J=7.2 Hz, H-2'), 8.2268 (d, J=7.2 Hz, H-3'), 8.1503 (d, J=8.5 Hz, H-9'), 7.8398 (t, J=8.5 Hz, H-8'), 7.6749 (d, J=6.54 Hz, H-7'), 6.2077 (q, J=6.3 Hz, H-12'), 1.4642 (d, J=6.3 Hz, H-13'); ESIMS m/z [M−H] 733.0.

S-MTPA ester of Compound 2 (2a): $^1$H NMR (600 MHz, $CDCl_3$) δ H 9.0661 (d, J=7.4 Hz, H-2'), 8.2226 (d, J=7.4 Hz, H-3'), 8.1107 (d, J=9.0 Hz, H-9'), 7.7821 (dd, J=9.0, 7.0 Hz, H-8'), 7.4820 (d, J=7.0 Hz, H-7'), 6.7208 (q, J=6.4 Hz, H-12'), 0.2577 (d, J=6.4 Hz, H-13'); ESIMS m/z [M−H] 733.2.

R-MPTA ester of Compound 2 (2b): $^1$H NMR (600 MHz, $CDCl_3$) δ H 9.0702 (d, J=7.4 Hz, H-2'), 8.2310 (d, J=7.4 Hz, H-3'), 8.1468 (dd, J=8.8 Hz, H-9'), 7.8482 (dd, J=8.8, 6.9 Hz, H-8'), 7.6516 (d, J=6.9 Hz, H-7'), 6.7446 (q, J=6.8 Hz, H-12'), 0.2452 (d, J=6.8 Hz, H-13'); ESIMS m/z $[M-H]^-$ 732.8.

S-MTPA ester of Compound 4 (4a): $^1$H NMR (600 MHz, $CDCl_3$) δ H 9.1782 (s, H-2'), 8.4088 (s, H-4'), 8.2189 (d, J=8.7 Hz, H-9'), 8.0346 (t, J=8.7 Hz, H-8'), 7.6273 (d, J=7.26 Hz, H-7'), 7.4198 (m, H-12'), 1.7915 (d, J=6.6 Hz, H-13'); ESIMS m/z $[M-H]^-$ 733.1.

R-MPTA ester of Compound 4 (4b): $^1$H NMR (600 MHz, $CDCl_3$) δ H 9.1890 (s, H-2'), 8.4171 (s, H-4'), 8.2166 (d, J=8.2 Hz, H-9'), 8.0350 (t, J=7.0 Hz, H-8'), 7.8905 (d, J=7.0 Hz, H-7'), 7.4577 (m, H-12'), 1.7543 (d, J=6.4 Hz, H-13'); ESIMS m/z $[M-H]^-$ 733.2.

S-MTPA ester of Compound 5 (5a): $^1$H NMR (600 MHz, $CDCl_3$) δ H 8.9125 (d, J=6.5 Hz, H-2'), 8.5408 (d, J=8.2 Hz, H-4'), 8.0195 (t, J=8.2 Hz, H-3'), 7.8040 (s, H-7'), 7.7920 (s, H-9'), 7.4318 (overlapped, H-12'), 1.8636 (d, J=6.4 Hz, H-13'); ESIMS m/z $[M-H]^-$ 733.0.

R-MPTA ester of Compound 5 (5b): $^1$H NMR (600 MHz, $CDCl_3$) δ H 8.9219 (d, J=6.2 Hz, H-2'), 8.5464 (d, J=8.5 Hz, H-4'), 8.0275 (t, J=8.5 Hz, H-3'), 7.8971 (s, H-7'), 7.8844 (s, H-9'), 7.4356 (overlapped, H-12'), 1.8202 (d, J=6.5 Hz, H-13'); ESIMS m/z $[M-H]^-$ 733.1.

S-MTPA ester of Compound 6 (6a): $^1$H NMR (600 MHz, $CDCl_3$) δ H 8.4381 (dd, J=7.6, 1.6 Hz, H-4'), 8.3300 (dd, J=6.9, 1.6 Hz, H-2'), 8.1671 (d, J=8.8 Hz, H-9'), 7.8912 (t, J=6.9 Hz, H-3'), 7.7465 (t, J=8.8 Hz, H-10'), 7.6186 (d, J=7.1 Hz, H-7'), 7.4842 (overlapped, H-12'), 1.8529 (d, J=6.1 Hz, H-13'); ESIMS m/z $[M-H]^-$ 732.9.

R-MPTA ester of Compound 6 (6b): $^1$H NMR (600 MHz, $CDCl_3$) δ H 8.4432 (d, J=8.3 Hz, H-4'), 8.3404 (d, J=6.7 Hz, H-2'), 8.1975 (d, J=6.9 Hz, H-9'), 7.8990 (t, J=8.3 Hz, H-3'), 7.8451 (t, J=6.9 Hz, H-10'), 7.8712 (d, J=8.4 Hz, H-7'), 7.5073 (overlapped, H-12'), 1.8137 (d, J=6.4 Hz, H-13'); ESIMS m/z $[M-H]^-$ 733.2.

Identification of Compound 3 Through Oxidation of Compound 1

The absolute structure of Compound 3 was identified by oxidizing Compound 1 to prepare Compound 3.

Compound 1 (1.5 mg, 2.89 μmol) was added in a 2 mL brown vial and dried with $N_2$ gas. Dess-Martin periodinane (7.4 mg, 17.36 μmol) was added to a vial containing Compound 1 and vacuum dried for 16 hours. Anhydrous MC (800 μL) was added and then stirred at room temperature for 18 hours. The reactant was diluted with MC and washed with 1:1 10% sodium thiosulfate ($Na_2$S203)/saturated sodium bicarbonate ($NaHCO_3$) and brine. The MC layer was dehydrated with anhydrous magnesium sulfate ($MgSO_4$), filtered, and concentrated under reduced pressure to obtain 0.8 mg of a mixture containing Compound 3. The mixture was subjected to normal phase HPLC (YMC-Pack SIL, 250 mm×4.6 mm, 5 μm; EtOAc/Hex/MeOH (v/v, 50:50:0.02); flow rate: 0.7 mL/min; detector: UV; wavelength: 254 nm) to obtain Compound 3 (0.3 mg, $t_R$ 19 min).

Oxidized Compound 1 (Compound 3):

$$[\alpha]_D^{25} -10\ (c\ 0.1,\ CHCl_3);$$

$^1$H NMR ($CDCl_3$, 600 MHz) δH 8.93 (d, J=7.5 Hz, H-2 and H-2'), 8.41 (d, J=8.3 Hz, H-9'), 8.17 (d, J=6.1 Hz, H-7'), 8.16 (d, J=7.3 Hz, H-9), 8.15 (d, J=8.0 Hz, H-4), 8.03 (t, J=8.3 Hz, H-8'), 7.92 (d, J=7.5 Hz, H-3'), 7.91 (t, J=8.0 Hz, H-3), 7.89 (t, J=8.6 Hz, H-8), 7.71 (d, J=8.6 Hz, H-7), 7.04 (q, J=7.1 Hz, H-12), 2.67 (s, H-13'), 2.02 (d, J=7.1 Hz, H-13); ESIMS m/z $[M-H]^-$ 515.2.

Hydrolysis of Compound 6

In order to confirm the absolute structure of C-12 of Compound 6 and to compare the specific optical rotation value with (R)-saphenic acid, Compound 6 was hydrolyzed with 6 N hydrogen chloride (HCl).

In a 4 mL brown vial containing Compound 6 (0.2 mg, 0.4 μmol), 200 μL of 6 N hydrogen chloride (HCl) was added and stirred at 80° C. for 30 minutes. The completion of the reaction was confirmed through LC-MS, and the hydrolysate of Compound 6 was concentrated with $N_2$ gas at 40° C.

Hydrolysate of Compound 6:

$$[\alpha]_D^{25} -10\ (c\ 0.1,\ CHCl_3);$$

$^1$H NMR ($CDCl_3$, 600 MHz) δH 8.98 (d, J=6.8 Hz, H-2), 8.52 (d, J=8.5 Hz, H-4), 8.19 (d, J=8.6 Hz, H-7), 8.05 (d, J=8.5 Hz, H-3), 7.98 (t, J=8.6 Hz, H-8), 7.94 (d, J=6.9 Hz, H-9), 5.83 (q, J=6.6 Hz, H-12), 1.80 (d, J=6.6 Hz, H-13); ESIMS m/z $[M+H]^+$ 269.1.

Semisynthetic Process of Compound 6 and Synthesis of Compound 7

Figure 10:
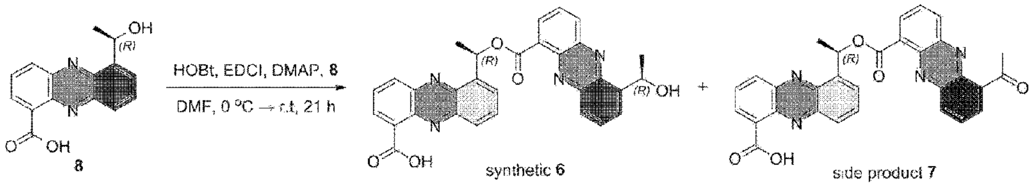
FIG. 10 illustrates a semi-synthetic process of Compound 6 and Reaction Scheme for producing Compound 7 therefrom.

As Compound 8, (R)-Saphenic acid (17.8 mg, 0.066 mmol) was dissolved in 1 mL of anhydrous dimethylformamide (DMF), and then sequentially added with hydroxybenzotriazole (HOBt, 10.2 mg, 0.066 mmol), 1-(3-diethylaminopropyl)-3-ethylcarbodiimide hydrochloride (EDCI·HCl, 12.6 mg, 0.066 mmol) and 4-dimethylamino pyridine (DMAP, 4.8 mg, 0.039 mmol) and stirred for 10 minutes at 0° C. Then, Compound 8 (21.2 mg, 0.079 mmol) was added and stirred at room temperature for 21 hours. The reactant was concentrated under reduced pressure, dissolved again in ethyl acetate (EtOAc), and washed three times with brine. The ethyl acetate layer was dehydrated with anhydrous magnesium sulfate ($MgSO_4$) and then concentrated under reduced pressure. The concentrated mixture was subjected to normal phase HPLC (YMC-pack SIL; 250×10 mm; 5 μm; EtOAc: Hex: MeOH (v/v, 50:50:0.1); flow rate: 2.5 mL/min; detector: RI) to obtain a mixture including the synthesized Compound 6 (6.9 mg, $t_R$ 22.5 min, yield: 19.4%) and a by-product, Compound 7. The mixture including Compound 7 was subjected to normal phase HPLC (YMC-pack SIL; 250×10 mm; 5 μm; EtOAc: Hex: MeOH (v/v, 40:60:0.1); flow rate: 2.5 mL/min; detector: RI) to separate and purify Compound 7 (0.4 mg, $t_R$ 30 min) (FIG. 10).

Semi-synthesized Compound 6:

$$[\alpha]_D^{25} -120\ (c\ 0.1,\ CHCl_3);$$

$^1$H NMR ($CDCl_3$, 600 MHz) δH 8.96 (d, J=7.0 Hz, H-2), 8.60 (d, J=8.6 Hz, H-4), 8.53 (d, J=7.0 Hz, H-7), 8.37 (d, J=8.7 Hz, H-4'), 8.32 (d, J=6.8 Hz, H-2'), 8.22 (d, J=8.7 Hz, H-9), 8.14 (d, J=8.5 Hz, H-9'), 8.04 (overlapped, H-3 and H-8), 7.89 (t, J=7.7 Hz, H-3'), 7.83 (t, J=7.0 Hz, H-8'), 7.79 (d, J=6.2 Hz, H-7'), 7.64 (q, J=6.8 Hz, H-12), 5.72 (m, H-12'), 4.81 (d, J=5.3 Hz, OH), 1.97 (d, J=6.5 Hz, H-13), 1.79 (d, J=6.6 Hz, H-13'); ESIMS m/z $[M+H]^+$ 541.2.

By-product, Compound 7:

$$[\alpha]_D^{25} -123\ (c\ 0.1,\ CHCl_3);$$

$^1$H NMR ($CDCl_3$, 600 MHz) δ H 9.00 (dd, J=7.1, 1.5 Hz, 1H), 8.62 (dd, J=8.6, 1.4 Hz, 1H), 8.49 (m, 1H), 8.43 (dd, J=8.7, 1.4 Hz, 1H), 8.39 (dd, J=8.6, 1.4 Hz, 1H), 8.36 (dd, J=6.8, 1.4 Hz, 1H), 8.25 (dd, J=8.7, 1.3 Hz, 1H), 8.22 (dd, J=6.8, 1.4 Hz, 1H), 8.06 (t, J=7.0 Hz, 1H), 8.05 (t, J=7.0 Hz, 1H), 7.93 (d, J=6.9 Hz, 1H), 7.92 (d, J=6.9 Hz, 1H), 7.66 (q, J=6.7 Hz, 1H), 3.08 (s, 3H), 1.99 (d, J=6.5 Hz, 3H); ESIMS m/z $[M+H]^+$ 539.1.

Computational Analysis for Structure Determination

Initial geometry optimization and conformational search were obtained using the Conflex 8 program (Rev. B, Conflex Corp., Tokyo, Japan). Optimization and calculations for ECD were performed using the Gaussian 16 program (Rev. B.01, Gaussian Corp., Connecticut, USA). The conformational search was calculated using the MMFF94s force field, and the search range was limited to 10 Kcal/mol. Compounds 1-2 and 4-5 were optimized in a Hatree-Fock/6-31+G(d,p), gas phase using a ground state method. The theoretical calculation of the ECD spectrum was calculated in a Hartree-Fock/6-31+G(d,p), gas phase, using a TD-SCF method. The ECD spectrum was simulated with the SpecDis (v. 1.71) program with a value of σ=0.30-0.50 eV. All calculated curves were adjusted to about +20-60 nm to match an experimental spectrum.

Determination of Stereostructures of Compounds 1 to 6

Compound 1 was isolated as a light green amorphous solid. The molecular formula of Compound 1 was confirmed to be m/z 541.1487 (calcd for 541.1488) corresponding to a $[M+Na]^+$ peak of $C_{30}H_{22}N_4O_5$ in HR-ESIMS. Compound 1 had the degree of unsaturation of 22. In 1H (Table 2) and HSQC spectra of Compound 1, there were confirmed 11 aromatic hydrogen signals [$\delta_H$ 8.95 (d, J=7.4 Hz, H-2'), 8.93 (dd, J=7.1, 1.4 Hz, H-2), 8.33 (dd, J=8.7, 1.4 Hz, H-4), 8.15 (dd, J=9.0, 1.4 Hz, H-9'), 8.13 (dd, J=8.7, 0.7 Hz, H-9), 8.02 (d, J=7.4 Hz, H-3'), 7.95 (dd, J=8.7, 7.1 Hz, H-3), 7.91 (dd, J=9.0, 6.8 Hz, H-8'), 7.86 (dd, J=8.7, 7.0 Hz, H-8), 7.77 (d, J=6.8 Hz, H-7'), and 7.67 (d, J=7.0 Hz, H-7)], one methine signal [$\delta_H$ 7.07 (q, J=7.0 Hz, H-12)], one oxygen-substituted methine signal [$\delta_H$ 5.24 (q, J=6.8 Hz, H-12')], and two methyl signals [$\delta_H$ 2.00 (d, J=7.0 Hz, H-13) and 1.12 (d, J=6.8 Hz, H-13')]. In $^{13}$C (Table 1) and HSQC spectra, there were confirmed 2 carbonyl carbon [$\delta_H$ 166.1 (C-11') and 166.0 (C-11)], 13 tertiary carbon [$\delta_H$ 150.9 (C-4'), 145.8 (C-6), 143.7 (C-11)]-6'), 142.9 (C-4a), 142.3 (C-5a), 141.3 (C-5a'), 140.5 (C-9a), 140.4 (C-9a'), 140.2 (C-10a, C-4a'), 140.0 (C-10a'), 125.0 (C-1), and 123.6 (C-1')], 11 aromatic carbon [$\delta_H$ 137.7 (C-2), 137.5 (C-2'), 135.6 (C-4), 133.4 (C-8'), 133.2 (C-8), 130.5 (C-3), 128.8 (C-7), 128.6 (C-3'), 127.9 (C-7'), 127.2 (C-9'), and 126.9 (C-9)], 2 methine [& 67.8 (C-12') and 34.1 (C-12)] and two methyl [$\delta_H$ 22.9 (C-13') and 21.4 (C-13)] signals. It was confirmed that characteristic UV spectra ($\lambda_{max}$ 253 and 371 nm), 1H and $^{13}$C NMR data [deshieled aromatic hydrogen signal in the range of $\delta_H$ 8.95-7.7 ppm, quaternary carbon signals containing eight nitrogens ($\delta_C$ 142.9, 142.3, 141.3, 140.5, 140.4, 140.2×2, and 140.0), two carboxylic acids ($\delta_H$ 166.1 and 166.0), two methines ($\delta_H$ 67.8 and 34.1), two methyl groups ($\delta_C$ 22.9 and 21.4)] were very similar to 1,6-disubstituted saphenic acid containing a phenazine ring, and Compound 1 was a dimer of saphenic acid. Through COSY spectrum analysis, six spin systems [H-2 ($\delta_H$ 8.93)/H-4 ($\delta_H$ 8.33), H-7 ($\delta_H$ 7.67)/H-9 ($\delta_H$ 8.13), H-12 ($\delta_H$ 7.07)/H-13 ($\delta_H$ 2.00), H-2' ($\delta_H$ 8.95)/H-3'($\delta_H$ 8.02), H-7' ($\delta_H$ 7.77)/H-9' ($\delta_H$ 8.15) and H-12' ($\delta_H$ 5.24)/H-13' ($\delta_H$ 1.12)] were confirmed. The positions of two carboxylic acids were determined through a correlation of HMBC [H-2 ($\delta_H$ 8.93) and C-11 ($\delta_C$ 166.0), H-2' ($\delta_H$ 8.95) and C-11'($\delta_C$ 166.1)]. It was confirmed that oxygen-substituted methine hydrogen H-12' ($\delta_H$ 5.24) and methyl hydrogen H-13' ($\delta_H$ 1.12) were linked to C-6' ($\delta_H$ 143.7) and C-7' ($\delta_C$ 127.9) through HMBC, respectively. The linkage of the two saphenic acids was from H-13 ($\delta_H$ 2.00) to C-6 ($\delta_C$ 145.8) of the C-ring and C-4' ($\delta_C$ 150.9) of the A'-ring, and confirmed through HMBC interconnection from H-7 ($\delta_H$ 7.67) of the C-ring and H-3' ($\delta_H$ 8.02) of the A'-ring to C-12 ($\delta_C$ 34.1). The 1H and $^{13}$C NMR spectra of Compound 1 were very similar to the previously reported phenazostatin C. The difference between the two compounds was that Compound 1 had carboxylic acid instead of carboxylic methyl ester and secondary alcohol at the position of C-6'.

The relative structure of Compound 1 could not be clearly determined due to coupling constants or insufficient signals in the NOESY data. The theoretically predictable structure of Compound 1 had four possibilities due to the presence of two chirals (C-12 and C-12'). First, the absolute structure of C-12' was determined using a modified Mosher's method. Compound 1 reacted with S- or R-MTPA ester 1a and 1b, respectively. The $^1$H NMR signals of 1a and 1b were determined through COSY spectrum analysis, and the $\Delta\delta_H$ values were calculated as $\delta_{S\text{-}ester}$-$\delta_{R\text{-}ester}$ (FIG. 3). Based on these results, it was confirmed that the absolute structure of C-12' was R. For the remaining two diastereomers (12R, 12'R and 12S, 12'R), theoretical ECD spectra were calculated using Gaussian 16 and compared with the measured ECD spectra. The actual ECD curve of Compound 1 was consistent with the 12R, 12'R-form isomers (FIG. 5). Therefore, the absolute structure of C-12 was determined to be R.

Compound 2 was isolated as a light green amorphous solid. The molecular formula of Compound 2 was $C_{30}H_{22}N_4O_5$, the same as Compound 1, based on HR-ESIMS data. The $^1$H and $^{13}$C NMR spectra of Compound 2 (Table 2) were also very similar to Compound 1, but only the H-12' signal ($\delta_H$ 4.95, m) was different, so that the planar structure of Compound 2 was the same as that of Compound 1. However, the specific optical rotation value of Compound 2 was opposite to that of Compound 1, and the ECD spectrum also showed the opposite curve [Compound 1:

$$[\alpha]_D^{25}\ 167\ (c\ 0.1,\ CHCl_3);$$

ECD ($CHCl_3$) $\lambda_{max}$ ($\Delta\varepsilon$) 242 (−38.20), 268 (+148.53), Compound 2:

$$[\alpha]_D^{25}\ +88\ (c\ 0.1,\ CHCl_3);$$

ECD ($CHCl_3$) $\lambda_{max}$ ($\Delta\varepsilon$) 247 (+15.90), 272 (−24.16)]. The similarities and differences between Compounds 1 and 2 showed that Compounds 1 and 2 were stereoisomers of each other. The absolute structure of C-12' of Compound 2 was confirmed to be an R-configuration using the modified Mosher's method in the same manner as Compound 1, and the absolute configuration of Compound 2 was confirmed to be a 12S, 12'R-configuration. Interestingly, the chemical shift values of H-13' of esterified 2a and 2b were $\delta_H$ 0.26 and $\delta_H$ 0.24, respectively, which were shifted to more 1.2 ppm upfield than 1a ($\delta_H$ 1.49) and 1b (& 1.46). This was caused by the unique steric hindrance due to the 12S-orientation (FIG. 5).

Compound 3 was a light green, amorphous solid, and was confirmed to have the molecular formula $C_{30}H_{20}N_4O_5$ (degree of unsaturation 23) based on HR-ESIMS data. The 1D NMR spectrum of Compound 3 (Table 2) was similar to those of Compounds 1 and 2. However, instead of the secondary alcohol that had been present in Compounds 1 and 2, an acetyl group (C-12', $\delta_C$ 200.3) was present. Accordingly, it was found that the structure of Compound 3 was the oxidized form of Compound 1 or 2. To determine the absolute structure of C-12, the specific optical rotation values of oxidized Compounds 1 and 3 were compared. It was confirmed that Compound 1 was oxidized and then purified using HPLC, and was the same as Compound 3 through LC-MS and $^1$H NMR spectra. The specific optical rotation value of oxidized Compound 1

$$[\alpha]_D^{25}\ -10)$$

showed the same negative value as Compound 3

$$[\alpha]_D^{25}\ -30).$$

Therefore, the absolute structure of C-12 was determined to be R.

Figure 2:
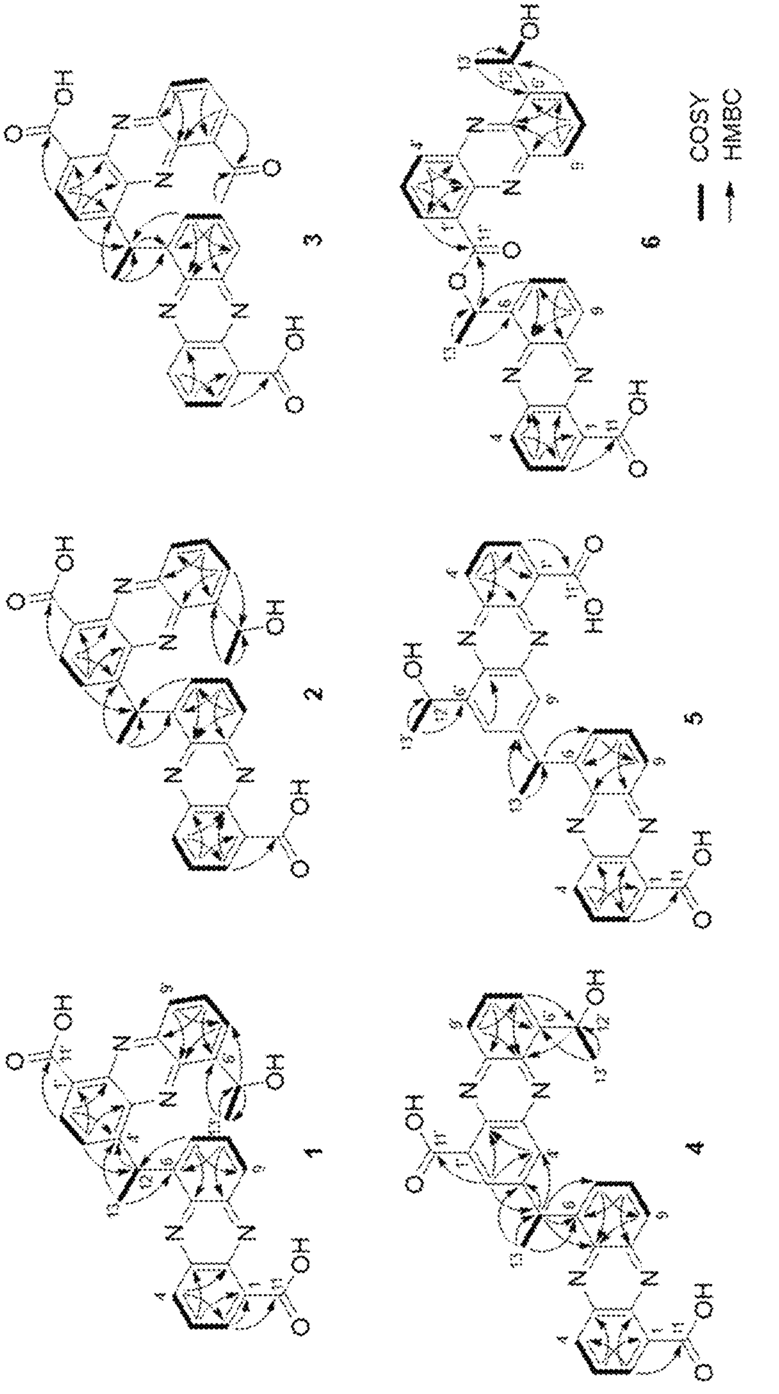
FIG. 2 illustrates the key of $^1$H-$^1$H COSY and HMBC correlations of Compounds 1 to 6.

Compounds 4-6 showed the same molecular formula $C_{30}H_{22}N_4O_5$ as Compounds 1 and 2 in HR-ESIMS data, but the splitting pattern of the $^1$H NMR spectrum was different from Compounds 1 and 2. This means that Compounds 4-6 were diastereomers of Compounds 1 and 2. In the $^1$H NMR spectrum of Compound 4, two singlet hydrogen signals ($\delta_H$ 9.16, s, H-2' and $\delta_H$ 8.41, s, H-4') were shown. The position of the carboxylic acid present in the A' ring was confirmed through HMBC correlation between H-2' ($\delta_H$ 9.16) and C-11' ($\delta_C$ 166.2). The linkage of the two saphenic acids was confirmed through HMBC signals from H-2' ($\delta_H$ 9.16) to C-12 ($\delta_C$ 39.7), and from H-12 ($\delta_H$ 5.97) to C-3' ($\delta_H$ 149.6), C-4' ($\delta_H$ 131.7), C-5a ($\delta_C$ 142.2), C-6($\delta_H$ 144.2), and C-7($\delta_C$ 129.1) (FIG. 2). Unlike Compound 4, Compound 5 showed overlapping two singlet hydrogen signals $\delta_H$ 7.90 (s, H-7' and H-9'). The positions of the two carboxylic acids were determined by HMBC correlation from H-2 ($\delta_H$ 8.93) to C-11 ($\delta_C$ 165.7) and from H-2' ($\delta_H$ 8.90) to C-11' ($\delta_H$ 165.9). Accordingly, the two overlapping singlet hydrogens belonged to the C' ring. The linkage between the two saphenic acids was confirmed through HMBC correlation from H-12 ($\delta_H$ 6.78) to C-7 ($\delta_H$ 128.5) and C-8' ($\delta_H$ 143.6). These results indicated that the C ring and the A' ring of Compound 4 were linked through C-12, while the C ring and the C' ring of Compound 5 were linked through C-12. The absolute structures of Compounds 4 and 5 were determined in the same manner as Compounds 1 and 2 (FIGS. 6 and 7). Accordingly, the absolute structures of Compounds 4 and 5 were determined as 12S, 12'R and 12R, 12'R, respectively.

Finally, Compound 6 was also determined through 1D and 2D NMR data analysis. In the $^1H$ NMR spectrum of Compound 6, the oxygen-substituted methine hydrogen ($\delta_H$ 7.65, H-12) was shifted to a downfield compared to the values of other Compounds 1-5. The linkage between the two saphenic acids was confirmed to form ester bond through HMBC connection signals from H-7 ($\delta_H$ 8.54) to C-12 ($\delta_H$ 70.0) and from H-12 ($\delta_H$ 7.65) and H-2' ($\delta_H$ 8.33) to C-11' ($\delta_C$ 165.8) of the carboxylic acid linked to the A' ring. The absolute structure of C-12' was confirmed to be R using a modified Mosher's method. To confirm the absolute structure of C-12, Compound 6 was hydrolyzed with 6 N hydrogen chloride (HCl), and then the specific optical rotation value of the hydrolysate was compared with that of Compound 8, (R)-saphenic acid. The specific optical rotation value $$[\alpha]_D^{25}\ -10$$

of the hydrolysate of Compound 6 showed the same negative value as (R)-saphenic acid (Compound 8)

$$[\alpha]_D^{25}\ -13.$$

As a result, the absolute structure of Compound 6 was determined to be 12R, 12'R.

Experimental Example 1. Evaluation of Anti-Neuroinflammatory Activity and Cell Viability of Diphenazine Compound NO generation to confirm anti-brain neuroinflammatory activity was evaluated by measuring a nitrite concentration in the medium using a Griess reagent, and the cell viability was evaluated using MTT assay. Briefly, BV-2 microglia were cultured in a Dulbecco's modified Eagle's medium (DMEM) supplemented with 5% heat-inactivated FBS and 50 g/mL of penicillin-streptomycin in a 5% $CO_2$ incubator at 37° C. A 96-well plate dispensed with pre-cultured cells ($2.5\times10^4$ cells/mL) was treated with compounds at various concentrations (10, 20, 50, and 100 μM) for 1 hour, and treated with LPS (200 ng/mL) and cultured for 24 hours. The supernatant was mixed with a Griess reagent and cultured at room temperature for 10 minutes. The nitrite concentration was determined using a sodium nitrite standard solution prepared in a cell culture medium. Absorbance was measured at a wavelength of 540 nm with a microplate reader. To evaluate the cell viability, the 96-well plate dispensed with cells ($2.5\times10^4$ cells/mL) was treated with compounds at various concentrations (10, 20, 50, and 100 μM) for 1 hour, and treated with LPS (200 ng/mL) and cultured for 24 hours. An MTT solution (0.5 mg/mL) was added to each well and cultured at 37° C. for 4 hours. The supernatant was removed, and the formed formazan crystals were dissolved in DMSO. The absorbance was measured at 550 nm using a microplate reader. To determine the $IC_{50}$ value of Compound 6, NO generation and MTT assay were performed in the same manner as described above, only with different concentrations (0.25, 0.5, and 1 μM) (Table 4). The experiment was repeated 3 times.

TABLE 4

| 1-9 NO generation inhibitory activity by activated microglia | | | | | | | | |
|---|---|---|---|---|---|---|---|---|
| | 1 | 2 | 3 | 4 | 5 | 6 | 8 | 9 |
| $IC_{50}$ (μM) | 165.6 | 90.2 | 34.7 | 125.5 | 27.4 | 0.3 | 16.3 | 23.5 |

Figure 8:
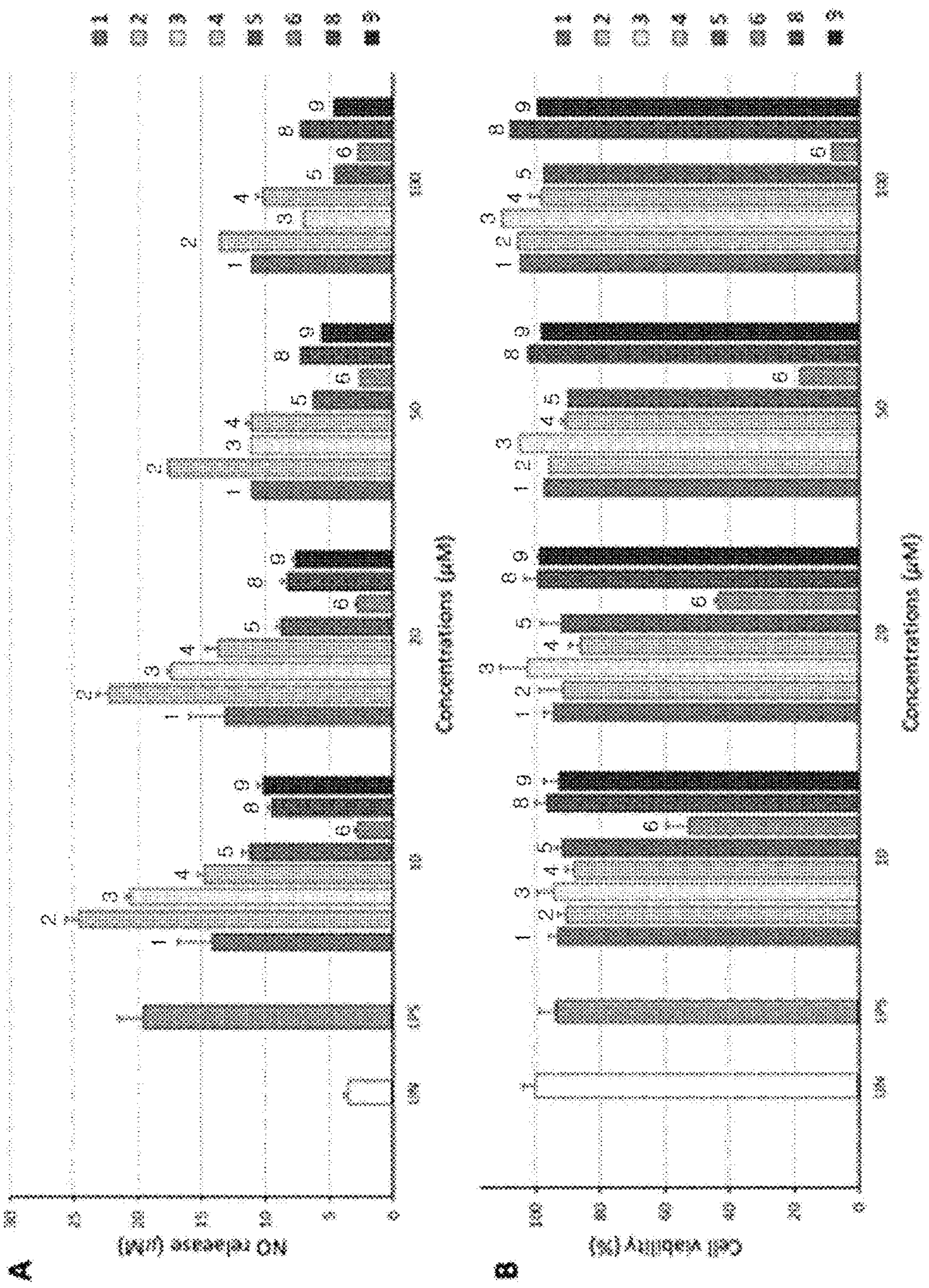
FIG. 8A illustrates an effect of Compounds 1 to 6, 8, and 9 on NO generation in LPS-induced BV-2 microglia
FIG. 8B illustrates cell viability of Compounds 1 to 6, 8, and 9.
Figure 9:
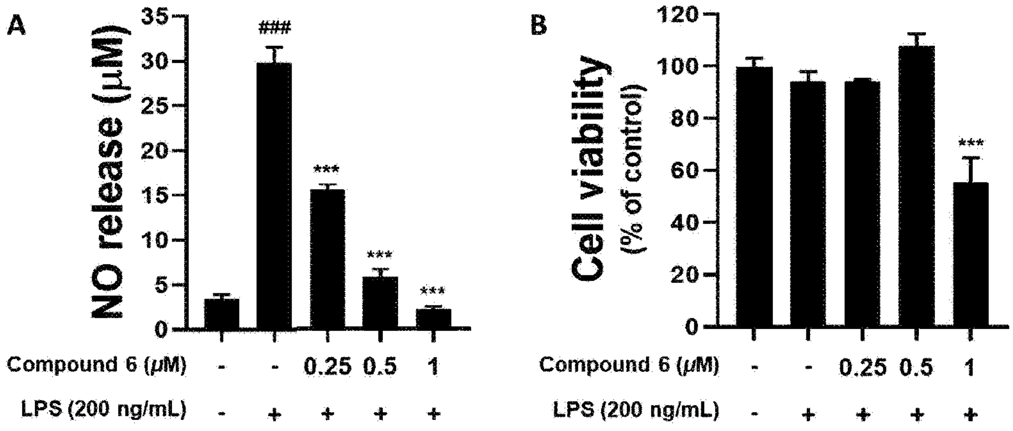
FIG. 9A illustrates an effect of Compound 6 on NO generation in LPS-induced BV-2 microglia and FIG. 9B illustrates cell viability of microglia treated with Compound 6.

The cytotoxicity against BV-2 microglia was measured using the MTT assay. All compounds consisted of saphenic acid moieties, but showed great differences in activity intensity depending on a linkage pattern of the two saphenic acids (FIG. 8 and Table 4). In particular, Compound 6 showed the best $IC_{50}$ value at a concentration of 0.3 μM (FIG. 9). This means that the activity of Compound 6 is at least 54 times (8, 16.3 μM) to at most 552 times (1, 165.6 μM) better than other compounds. Compounds 1 and 2 were diastereomeric to each other, and Compound 3 was the oxidized form of Compound 1, but Compound 3 (34.7 μM) was 5 times stronger than Compound 1 (165.6 μM), and Compound 2 (90.2 μM) showed approximately two times stronger activity than Compound 1 (165.6 μM) (Table 4). As described above, it was found that unique steric hindrance differences caused by the stereostructure of C-12 (FIG. 5) affected activity. In a cell viability test, Compound 6 showed strong cytotoxicity up to a concentration of 1 μM.

Since Compound 6 showed anti-brain neuroinflammatory activity differently from other compounds, it was attempted to synthesize Compound 6 for additional physiological activity experiments. Semi-synthesized 6 was synthesized through EDCI coupling reaction using saphenic acid (Compound 8), and showed the same 1H, $^{13}C$, and MS spectra as natural product 6. During the purification process of Compound 6, Compound 7, a by-product of the oxidized form of Compound 6, was also obtained (FIG. 10). The $^1H$ NMR spectrum of Compound 7 was similar to that of Compound 6, but the methyl signal ($\delta_H$ 1.97, d, 3H) linked to the oxygen-substituted methine ($\delta_H$ 5.72, 1H) was changed into the signal ($\delta_H$ 3.08, s, 3H) of the acetyl group. In a LR-ESIMS spectrum, it was confirmed that the molecular weight of Compound 7 was 516, which was lower than that of Compound 6, and indicated that Compound 7 was an oxidized form of Compound 6. Accordingly, the structure of Compound 7 was determined as (R)-6-(1-((6-acetylphenazine-1-carbonyl)oxy)ethyl)phenazine-1-carboxylic acid.

Experimental Example 2. Anticancer Activity of Diphenazine Compounds

A cytotoxicity test was evaluated using sulforhodamine B (SRB) assay on six human cancer cell lines. Human cancer cell lines, ACHN (kidney), NCI-H23 (lung), PC-3 (prostate), NUGC-3 (stomach), MDA-MB-231 (breast), and HCT-15 (colon) were purchased from American Type Culture Collection (ATCC). Cells were cultured in a RPMI 1640 medium added with 10% fetal bovine serum (FBS) at 37° C. in a 5% $CO_2$ incubator. The cells ($8\times10^3$ cells/well) were dispensed into a 96-well plate, cultured for one day, and then treated with Compounds 1-8 dissolved in 0.1% DMSO, (R)-(6-(1-((2-aminobenzoyl)oxy)ethyl)phenazine-1-carboxylic acid as Compound 9, and adriamycin as a positive control group. The cells were cultured for 48 hours, fixed with 50% trichloroacetic acid (50 μg/mL) and stained with 0.4% surfohodamine B dissolved in 1% acetic acid. Non-stained cells were removed by washing with 1% acetic acid, and cells bound to a protein were extracted with 10 mM Tris base (pH 10.5) to measure the optical density. Absorbance was measured at 540 nm using a microplate reader, and $GI_{50}$ values were calculated using GraphPad Prism 4.0.

The tested compounds did not show cytotoxicity, but only Compound 6 and Compound 7, the oxidized form of Compound 6, showed cytotoxicity 2 to 19 times stronger than the positive control group adriamycin. In addition, Compound 6 showed 4 to 6 times stronger activity than Compound 7. In particular, gastric cancer cells NUGC-3 showed the strongest activity with a $GI_{50}$ value of 7.7 nM, which was 19 times stronger than Adriamycin. These results indicated that the hydroxyl group of the C' ring and the ester bond played a major role in activity. Table 5 below showed the cytotoxicity results of Compounds 1-9 against six types of cancer cells ($GI_{50}$=μM).

TABLE 5

| | Cancer cell line | | | | | |
|---|---|---|---|---|---|---|
| | ACHN | NCI-H23 | PC-3 | NUGC-3 | MDA-MB-231 | HCT-15 |
| 1 | >10 | >10 | >10 | >10 | >10 | >10 |
| 2 | >10 | >10 | >10 | >10 | >10 | >10 |
| 3 | >10 | >10 | >10 | >10 | >10 | >10 |
| 4 | >10 | >10 | >10 | >10 | >10 | >10 |
| 5 | >10 | >10 | >10 | >10 | >10 | >10 |
| 6 | 0.0135 | 0.0096 | 0.0096 | 0.0077 | 0.0096 | 0.0096 |
| 7 | 0.0717 | 0.0426 | 0.0465 | 0.0349 | 0.0523 | 0.0601 |
| 8 | >10 | >10 | >10 | >10 | >10 | >10 |
| 9 | >10 | >10 | >10 | >10 | >10 | >10 |
| ADR[a] | 0.17 | 0.16 | 0.16 | 0.15 | 0.15 | 0.17 |

[a]Adriamycin (ADR) was used as a positive control group.

As described above, specific parts of the present invention have been described in detail, and it will be apparent to those skilled in the art that these specific techniques are merely preferred embodiments, and the scope of the present invention is not limited thereto. Therefore, the substantial scope of the present invention will be defined by the appended claims and their equivalents.

[Accession number]

Depositary Authority Name: Korea Research Institute of Bioscience and Biotechnology Accession number: KCTC 13270BP Accession Date: 20181120.

The invention claimed is:

1. A method for preventing or treating cancer-related diseases comprising administering a diphenazine compound of Chemical Formula 1 below, an enantiomer thereof, or a pharmaceutically acceptable salt thereof to a subject in need thereof:

[Chemical Formula 1]

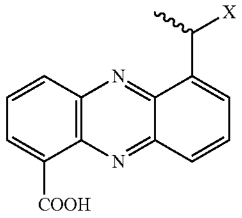

wherein,

X is

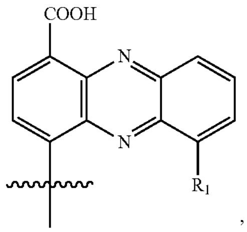

,

-continued

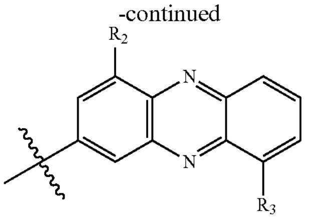

or

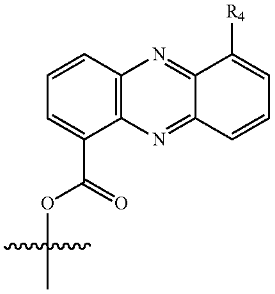

, $R_1$, $R_2$, $R_3$, and $R_4$ are each independently

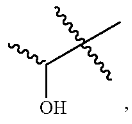 [SMILES: *C(C)O]

,

—OH, —COH, —COOH, —$COOCH_3$, or —$COCH_3$.

2. A method for preventing or treating neuroinflammatory diseases comprising administering a diphenazine compound of Chemical Formula 1 below, a enantiomer thereof, or a pharmaceutically acceptable salt thereof to a subject in need thereof:

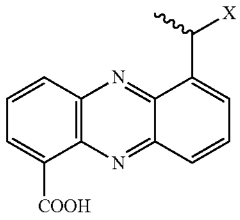

wherein,
X is

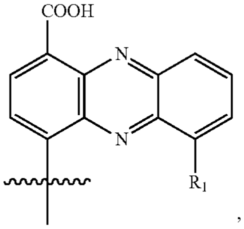

,

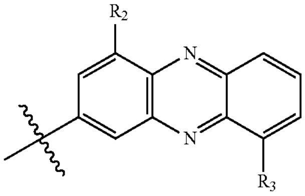

or

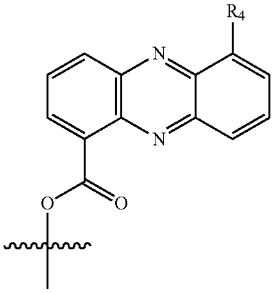

, $R_1$, $R_2$, $R_3$, and $R_4$ are each independently

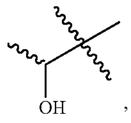

,

—OH, —COH, —COOH, —$COOCH_3$, or —$COCH_3$.

3. The method for preventing or treating cancer-related diseases of claim 1, wherein the cancer-related disease is at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myeloid leukemia, acute lymphocytic leukemia, basal cell cancer, ovarian cancer, ovarian epithelial cancer, ovarian germ cell cancer, male breast cancer, brain cancer, pituitary adenoma, multiple myeloma, gallbladder cancer, biliary tract cancer, colorectal cancer, chronic myeloid leukemia, chronic lymphocytic leukemia, retinoblastoma, choroidal melanoma, diffuse large B-cell lymphoma, ampullar of vater cancer, bladder cancer, peritoneal cancer, parathyroid cancer, adrenal cancer, sinonasal cancer, non-small cell lung cancer, non-Hodgkin lymphoma, tongue cancer, astrocytoma, small cell lung cancer, childhood brain cancer, childhood lymphoma, childhood leukemia, small intestine cancer, meningioma, esophageal cancer, glioma, neuroblastoma, renal pelvis cancer, kidney cancer, heart cancer, duodenal cancer, malignant soft tissue cancer, malignant bone cancer, malignant lymphoma, malignant mesothelioma, malignant melanoma, eye cancer, vulvar cancer, ureteral cancer, urethral cancer, cancer of unknown primary site, gastric lymphoma, stomach cancer, gastric carcinoid, gastrointestinal cancer, Wilms cancer, breast cancer, sarcoma, penile cancer, pharyngeal cancer, gestational trophoblastic disease, cervical cancer, endometrial cancer, uterine sarcoma, prostate cancer, metastatic bone cancer, metastatic brain cancer, mediastinal cancer, mesothelioma, rectal cancer, rectal carcinoid, vaginal cancer, spinal cord cancer, acoustic neuroma, pancreatic cancer, salivary gland cancer, Kaposi's sarcoma, Paget's disease, tonsillar cancer, squamous cell carcinoma, lung adenocarcinoma, lung cancer, lung squamous cell carcinoma, skin cancer, anal cancer, rhabdomyosarcoma, laryngeal cancer, pleural cancer, and thymic cancer.

4. The method for preventing or treating cancer-related diseases of claim 1, wherein X is

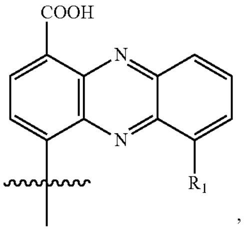

, and $R_1$ is

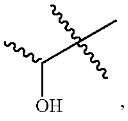 [SMILES: *C(C)O]

,

—COOH, or —$COCH_3$.

5. The method for preventing or treating cancer-related diseases of claim 1, wherein X is

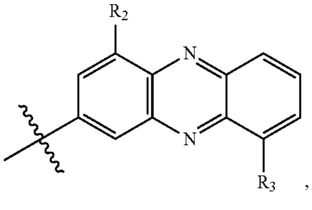

, and $R_2$ and $R_3$ are each independently

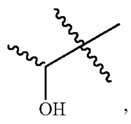

,

—COOH, or —$COCH_3$.

6. The method for preventing or treating cancer-related diseases of claim 1, wherein X is

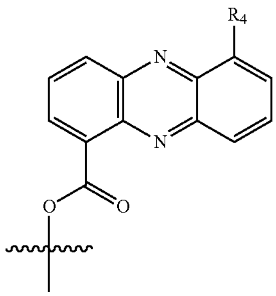

, and $R_4$ is

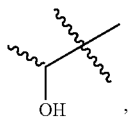

,

—COOH, or —$COCH_3$.

7. The method for preventing or treating cancer-related diseases of claim 1, wherein the compound of Chemical Formula 1 is any one selected from the group consisting of the following compounds:

4-((R)-1-(6-carboxyphenazin-1-yl)ethyl)-6-((R)-1-hydroxyethyl) phenazine-1-carboxylic acid;

4-((S)-1-(6-carboxyphenazin-1-yl)ethyl)-6-((R)-1-hydroxyethyl) phenazine-1-carboxylic acid;

(R)-6-acetyl-4-(1-(6-carboxyphenazin-1-yl)ethyl) phenazine-1-carboxylic acid;

3-((S)-1-(6-carboxyphenazin-1-yl)ethyl)-6-((R)-1-hydroxyethyl)phenazine-1-carboxylic acid;

8-((R)-1-(6-carboxyphenazin-1-yl)ethyl)-6-((R)-1-hydroxyethyl)phenazine-1-carboxylic acid;

6-((R)-1-((6-((R)-1-hydroxyethyl)phenazine-1-carbonyl) oxy)ethyl)phenazine-1-carboxylic acid; and (R)-6-(1-((6-acetylphenazine-1-carbonyl)oxy)ethyl) phenazine-1-carboxylic acid.

8. The method for preventing or treating cancer-related diseases of claim 1, wherein the diphenazine compound of Chemical Formula 1 is isolated from a Cystobasidium laryngis IV17-028 KCTC 13720BP strain or a culture medium thereof.

9. The method for preventing or treating neuroinflammatory diseases of claim 2, wherein X is

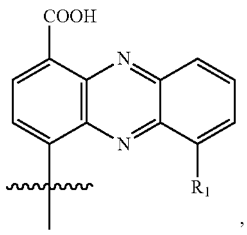

, and $R_1$ is

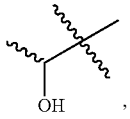 [SMILES: *C(C)O]

,

—COOH, or —$COCH_3$.

10. The method for preventing or treating neuroinflammatory diseases of claim 2, wherein X is

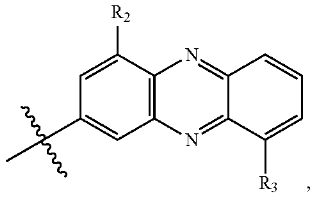

, and $R_2$ and $R_3$ are each independently

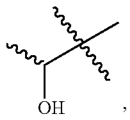 [SMILES: *C(C)O]

,

—COOH, or —$COCH_3$.

11. The method for preventing or treating neuroinflammatory diseases of claim 2, wherein X is

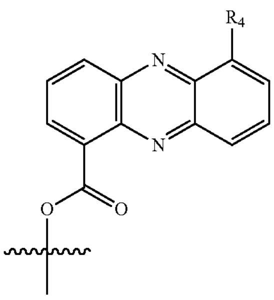

, and $R_4$ is

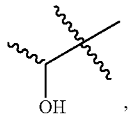

,

—COOH, or —$COCH_3$.

12. The method for preventing or treating neuroinflammatory diseases of claim 2, wherein the compound of Chemical Formula 1 is any one selected from the group consisting of the following compounds:

4-((R)-1-(6-carboxyphenazin-1-yl)ethyl)-6-((R)-1-hydroxyethyl)phenazine-1-carboxylic acid;

4-((S)-1-(6-carboxyphenazin-1-yl)ethyl)-6-((R)-1-hydroxyethyl)phenazine-1-carboxylic acid;

(R)-6-acetyl-4-(1-(6-carboxyphenazin-1-yl)ethyl)phenazine-1-carboxylic acid;

3-((S)-1-(6-carboxyphenazin-1-yl)ethyl)-6-((R)-1-hydroxyethyl)phenazine-1-carboxylic acid;

8-((R)-1-(6-carboxyphenazin-1-yl)ethyl)-6-((R)-1-hydroxyethyl)phenazine-1-carboxylic acid;

6-((R)-1-((6-((R)-1-hydroxyethyl)phenazine-1-carbonyl)oxy)ethyl)phenazine-1-carboxylic acid; and (R)-6-(1-((6-acetylphenazine-1-carbonyl)oxy)ethyl)phenazine-1-carboxylic acid.

13. The method for preventing or treating neuroinflammatory diseases of claim 2, wherein the diphenazine compound of Chemical Formula 1 is isolated from a Cystobasidium laryngis IV17-028 KCTC 13720BP strain or a culture medium thereof.

* * * * *